US010251852B2

(12) United States Patent
Trapnell et al.

(10) Patent No.: US 10,251,852 B2
(45) Date of Patent: Apr. 9, 2019

(54) COMPOSITION AND METHODS FOR TREATMENT OF LUNG DISORDERS CHARACTERIZED BY CHOLESTEROL DYSREGULATION

(71) Applicant: Children's Hospital Medical Center, Cincinnati, OH (US)

(72) Inventors: Bruce Trapnell, Mariemont, OH (US); Tony Sallese, Eaton, OH (US); Brenna Carey, Cincinnati, OH (US); Takuji Suzuki, Midori (JP)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 15/484,284

(22) Filed: Apr. 11, 2017

(65) Prior Publication Data

US 2018/0000758 A1 Jan. 4, 2018

Related U.S. Application Data

(60) Provisional application No. 62/321,892, filed on Apr. 13, 2016.

(51) Int. Cl.

| | |
|---|---|
| ***A61K 31/18*** | (2006.01) |
| ***A61K 9/00*** | (2006.01) |
| ***A61K 31/4439*** | (2006.01) |
| ***A61K 47/10*** | (2017.01) |
| ***A61K 47/26*** | (2006.01) |
| ***A61K 9/08*** | (2006.01) |

(52) U.S. Cl.

CPC .............. *A61K 31/18* (2013.01); *A61K 9/007* (2013.01); *A61K 9/0053* (2013.01); *A61K 9/08* (2013.01); *A61K 31/4439* (2013.01); *A61K 47/10* (2013.01); *A61K 47/26* (2013.01)

(58) Field of Classification Search

CPC ........ A61K 31/18; A61K 47/10; A61K 47/26; A61K 9/08; A61K 31/4439; A61K 9/007; A61K 9/0053

See application file for complete search history.

(56) References Cited

U.S. PATENT DOCUMENTS

2011/0053986 A1* 3/2011 Finch .................. A61K 9/0075 514/342
2013/0203666 A1* 8/2013 Niemoeller ............ A61K 38/26 514/7.2

OTHER PUBLICATIONS

Wright et al (Mol Endocrinol, Nov. 2014, 28(11):1756-1768) (Year: 2014).*

Abe, A., et al., "Lysosomal Phospholipase A2 is Selectively Expressed in Alveolar Macrophages", J Biol Chem, Oct. 8, 2004, 279(41):42605-42611, 8 pgs.

(Continued)

*Primary Examiner* — Angela C Brown-Pettigrew

(74) *Attorney, Agent, or Firm* — Frost Brown Todd LLC

(57) ABSTRACT

Disclosed are compositions and methods for treating a condition characterized by a dysregulation in macrophage lipid homeostasis. The disclosed methods may include the administration of an agent selected from a PPARγ agonist, a LXR agonist, or a combination thereof. In certain aspects, the disclosed methods may be used to prevent, treat, or ameliorate conditions such as pulmonary alveolar proteinosis (PAP) and/or symptoms associated therewith.

6 Claims, 18 Drawing Sheets

(56) References Cited

OTHER PUBLICATIONS

Baker, A.D., et al., "PPARγ Regulates the Expression of Cholesterol Metabolism Genes in Alveolar Macrophages", Biochem Biophys Res Commun, 2010, 393:682-687, 6 pgs.
Baker, A.D., et al., "Targeted PPARγ Deficiency in Alveolar Macrophages Disrupts Surfactant Catabolism", J Lipid Res, 2010, 51:1325-1331, 7 pgs.
Berclaz, P.Y., et al., "GM-CSF, Via PU.1, Regulates Alveolar Macrophage FcγR-Mediated Phagocytosis and the IL-18/IFN-γ-Mediated Molecular Connection Between Innate and Adaptive Immunity in the Lung", Blood, Dec. 1, 2002, 100(12): 4193-4200, 8 pgs.
Bonfield, T.L., et al., "Peroxisome Proliferator-Activated Receptor-γ is Deficient in Alveolar Macrophages from Patients with Alveolar Proteinosis", Am J Respir Cell Mol Biol 2003, 29:677-682, 6 pgs.
Bridges, J.P., et al., "Orphan G Protein-Coupled Receptor GPR116 Regulates Pulmonary Surfactant Pool Size", Am J Respir Cell Mol Biol, 2013, 49:348-357, 10 pgs.
Cavelier, C., et al., "Lipid Efflux By the ATP-binding Cassette Transporters ABCA1 and ABCG1", Biochim Biophys Acta, 2006, 1761: 655-666, 12 pgs.
Chandra, et al., "Structure of the Intact PPAR-γ-RXR-α-Nuclear Receptor Complex on DNA," Nature, Nov. 20, 2008, 456(20):350-356, 9 pgs.
Daniel, J., et al., "*Mycobacterium Tuberculosis* Uses Host Triacylglycerol to Accumulate Lipid Droplets and Acquires a Dormancy-Like Phenotype in Lipid-Loaded Macrophages", PLoS Pathog, Jun. 23, 2011, 7(6):1-17, 17 pgs.
Daniels, C. B., et al., "Body Temperature Alters the Lipid Composition of Pulmonary Surfactant in the Lizard *Ctenophorus Nuchalis*", Exp Lung Res, 1990, 16(5):435-449, 15 pgs.
Ditiatkovski, M., et al., "GM-CSF Deficiency Reduces Macrophage PPAR-γ Expression and Aggravates Atherosclerosis in ApoE-Deficient Mice", Arterioscler Thromb Vasc Biol, Oct. 2006, 26: 2337-2344, 17 pgs.
Doyle, I. R., et al., "Quantity and Structure of Surfactant Proteins Vary Among Patients with Alveolar Proteinosis", Am J Respir Crit Care Med, 1998, 157:658-664, 7 pgs.
Dranoff, G., et al., "Involvement of Granulocyte-Macrophage Colony-Stimulating Factor in Pulmonary Homeostasis", Science, Apr. 29, 1994, 264(5159):713-716, 4 pgs.
Forbes, A., et al., "Alveolar Macrophage Depletion is Associated with Increased Surfactant Pool Sizes in Adult Rats", J Appl Physiol, 2007, 103:637-645, 9 pgs.
Gennaro, A.R., Ed., "Remington's Pharmaceutical Sciences", 18th Ed., Mack Publ. Co., Easton, PA, 1990, 8 pgs., Table of Contents only.
Golde, D. W., "Alveolar Proteinosis and the Overfed Macrophage" [editorial], Chest, Aug. 1979, 769(2):119-120, 2 pgs.
Griese, M., "Pulmonary Surfactant in Health and Human Lung Diseases: State of the Art", Eur Respir J, 1999, 13: 1455-1476, 22 pgs.
Griffin, J. E., et al., "Cholesterol Catabolism by *Mycobacterium tuberculosis* Requires Transcriptional and Metabolic Adaptations", Chem Biol, Feb. 24, 2012, 19: 218-227, 10 pgs.
Guilliams, M., et al., "Alveolar Macrophages Develop from Fetal Monocytes That Differentiate into Long-Lived Cells in the First Week of Life Via GM-CSF", J Exp Med, Sep. 16, 2013, 210(10):1977-1992, 16 pgs.
Gurel, O., et al., "Macrophage and Type II Cell Catabolism of SP-A and Saturated Phosphatidylcholine in Mouse Lungs", Am J Physiol Lung Cell Mol Physiol, 2001, 280: L1266-1272, 7 pgs.
Hamilton, J. A., "Colony-Stimulating Factors in Inflammation and Autoimmunity", Nat Rev Immunol, Jul. 2008, 8:533-544, 13 pgs.
Hawgood, S., et al., "The Pulmonary Collectins and Surfactant Metabolism", Annu Rev Physiol, 2001, 63:495-519, 29 pgs.
Igarashi, M., et al., "The Critical Role of Neutral Cholesterol Ester Hydrolase 1 in Cholesterol Removal from Human Macrophages", Circ Res, 2010, 107: 1387-1395, 9 pgs.
Ikegami, M., et al., "Surfactant Metabolism in Transgenic Mice After Granulocyte Macrophage-Colony Stimulating Factor Ablation", Am J Physiol, 1996, 270:L650-658, 9 pgs.
Ishii, I., et al., "β-VLDL-Induced Cholesterol Ester Deposition in Macrophages May Be Regulated by Neutral Cholesterol Esterase Activity", Arteriosclerosis and Thrombosis: A Journal of Vascular Biology/American Heart Association, 1992, 12:1139-1145, 7 pgs.
Kernan, W. N., et al., "Pioglitazone After Ischemic Stroke or Transient Ischemic Attack", New England Journal of Medicine, Apr. 6, 2016, 374:1321-1331, 11 pgs.
Kitamura, T., et al., "Idiopathic Pulmonary Alveolar Proteinosis as an Autoimmune Disease with Neutralizing Antibody Against Granulocyte/Macrophage Colony-Stimulating Factor", J Exp Med, Sep. 6, 1999, 190(6):875-880, 6 pgs.
Kritharides, L., et al., "Cholesterol Metabolism and Efflux in Human THP-1 Macrophages", Arterioscler Thromb Vasc Biol, Oct. 1998, 18:1589-1599, 12 pgs.
Laffitte, B. A., et al., "LXRs Control Lipid-Inducible Expression of the Apolipoprotein E Gene in Macrophages and Adipocytes", Proc Natl Acad Sci USA, Jan. 16, 2001, 98(2): 507-512, 6 pgs.
Lehmann, J. M., et al., "An Antidiabetic Thiazolidinedione is a High Affinity Ligand for Peroxisome Proliferator-Activated Receptor γ (PPARγ)*", J Biol Chem, Jun. 2, 1995, 270(22): 12953-12956, 4 pgs.
Levin, N. et al., "Macrophage Liver X Receptor is Required for Antiatherogenic Activity of LXR Agonists", Arterioscler Thromb Vasc Biol, 2005, 25:135-142, 9 pgs.
Martinez-Moczygemba, M. et al., "Pulmonary Alveolar Proteinosis Caused by Deletion of the GM-CSFRα Gene in the X Chromosome Pseudoautosomal Region 1", J Exp Med, Oct. 27, 2008, 205(12):2711-2716, 6 pgs.
Mehlem, A., et al., "Imaging of Neutral Lipids by Oil Red 0 for Analyzing the Metabolic Status in Health and Disease", Nat Protoc, 2013, 8:1149-1154, 6 pgs.
Okazaki, H., et al., "Identification of Neutral Cholesterol Ester Hydrolase, a Key Enzyme Removing Cholesterol from Macrophages", J Biol Chem, 2008, 283(48):33357-33364, 8 pgs.
Ouimet, M., et al, "Autophagy Regulates Cholesterol Efflux from Macrophage Foam Cells Via Lysosomal Acid Lipase", Cell Metab, 2011, 13:655-667, 25 pgs.
Out, R., et al., "Macrophage ABCG1 Deletion Disrupts Lipid Homeostasis in Alveloar Macrophages and Moderately Influences Atherosclerotic Lesion Development in LDL Receptor-Deficient Mice", Arterioscler Thromb Vasc Biol, Oct. 2006, 26:2295-2300, 7 pgs.
Ozasa, H., et al., "Pioglitazone Enhances Cholesterol Efflux from Macrophages by Increasing ABCA1/ABCG1 Expressions Via PPARγ /LXRα Pathway: Findings From In Vitro and Ex Vivo Studies", Atherosclerosis, 2011, 219:141-150, 10 pgs.
Pandey, A. K., et al., "Mycobacterial Persistence Requires the Utilization of Host Cholesterol", Proc Natl Acad Sci USA, Mar. 18, 2008, 105(11):4376-4380, 5 pgs.
Perez-Gil, J., et al., "Pulmonary Surfactant Pathophysiology: Current Models and Open Questions", Physiology, Jun. 2010, 25:132-141, 10 pgs.
Pison, U., et al., "Specific Binding of Surfactant Apoprotein SP-A to Rat Alveloar Macrophages", Am J Physiol, 1992, 262: L412-417, 6 pgs.
Ramirez-Zacarias, J. L., et al., "Quantitation of Adipose Conversion and Triglycerides by Staining Intracytoplasmic Lipids with Oil Red O", Histochemistry, 1992, 97:493-497, 5 pgs.
Robb, L., et al., "Hematopoietic and Lung Abnormalities in Mice with a Null Mutation of the Common β Subunit of the receptors for Granulocyte-Macrophage Colony-Stimulating Factor and Interleukins 3 and 5", Proc Natl Acad Sci USA, Oct. 1995, 92:9565-9569, 5 pgs.
Sakagami, T. et al., "Human GM-CSF Autoantibodies and Reproduction of Pulmonary Alveolar Proteinosis", N Engl J Med, Dec. 31, 2009, 361:2679-2681, 3 pgs.
Sakagami, T., et al., "Patient-Derived Granulocyte/Macrophage Colony-Stimulating Factor Autoantibodies Reproduce Pulmonary Alveloar Proteinosis in Nonhuman Primates", Am J Respir Crit Care Med, 2010, 182:49-61, 13 pgs.

(56) References Cited

OTHER PUBLICATIONS

Schneider, C., et al., "Induction of the Nuclear Receptor PPAR-β by the Cytokine GM-CSF is Critical for the Differentiation of Fetal Monocytes into Alveolar Macrophages", Nature Immunology, Nov. 2014, 15(11):1026-1037, 15 pgs.
Stanley, E., et al., "Granulocyte/Macrophage Colony-Stimulating Factor-Deficient Mice Show No Major Perturbation of Hematopoiesis but Develop a Characteristic Pulmonary Pathology", Proc Natl Acad Sci USA, Jun. 1994, 91:5592-5596, 5 pgs.
Suzuki, T., et al., "Familial Pulmonary Alveolar Proteinosis Caused by Mutations in CSF2RA", J Exp Med, Nov. 24, 2008, 205(12):2703-2710, 8 pgs.
Suzuki, T., et al., "Hereditary Pulmonary Alveolar Proteinosis Caused by Recessive CSF2RB Mutations", Eur Respir J, 2011, 37(1):201-204, 4 pgs.
Suzuki, T., et al, "Hereditary Pulmonary Alveolar Proteinosis: Pathogenesis, Presentations, Diagnosis, and Therapy", Am J Respir Crit Care Med, 2010, 182:1292-1304, 13 pgs.
Suzuki, T., et al., "Pulmonary Macrophage Transplation Therapy", Nature, Oct. 23, 2014, 514:450-454, 37 pgs.
Tanaka, T., et al., "Adult-Onset Hereditary Pulmonary Alveolar Proteinosis Caused by a Single-Base Deletion in CSF2RB", J Med Genet, 2011, 48:205-209, 5 pgs.
Tazawa, R., et al., "Inhaled Granulocyte/Macrophage-Colony Stimulating Factor as Therapy for Pulmonary Alveolar Proteinosis", Am J Respir Crit Care Med, 2010, 181:1345-1354, 10 pgs.
Thomassen, M. J., et al., "ABCG1 is Deficient in Alveolar Macrophages of GM-CSF Knockout Mice and Patients with Pulmonary Alveolar Proteinosis", J Lipid Res 48, 2007, 2762-2768, 7 pgs.
Trapnell, B. C., et al. "Pulmonary Alveolar Proteinosis Syndrome,"from Murray & Nadel's Textbook of Respiratory Medicine (eds. Mason R.C. Broaddus V.C., Ernst J.D., King T.E., Lazarus S.C., Murray J.F., Nadel J.A., Slutsky A., Gotway M.) Ch. 70, Elsevier Health Sciences, 2015, 27 pgs.
Trapnell, B. C., et al., "Pulmonary Alveolar Proteinosis", N Engl J Med, Dec. 25, 2003, 349: 2527-2539, 13 pgs.
Uchida K., et al., "GM-CSF Autoantibodies and Neutrophil Dysfunction in Pulmonary Alveolar Proteinosis", N Engl J Med, Feb. 8, 2007, 356:567-579, 13 pgs.
Veldhuizen, R., et al., "The Role of Lipids in Pulmonary Surfactant", Biochim Biophys Acta, 1998, 1408:90-108, 19 pgs.
Venkateswaran, A., et al., "Control of Cellular Cholesterol Efflux by the Nuclear Oxysterol Receptor LXRα", Proc Natl Acad Sci USA, Oct. 24, 2000, 97(22):12097-12102, 6 pgs.
White, T., et al., "High-Resolution Separation and Quantification of Neutral Lipid and Phospholipid Species in Mammalian Cells and Sera by Multi-One-Dimensional Thin-Layer Chromatography"Anal Biochem, 1998, 258:109-117, 9 pgs.
Willy, P.J., et al., "LXR, a Nuclear Receptor That Defines a Distinct Retinoid Response Pathway", Genes Dev., 1995, 9:1033-45, 14 pgs.
Yoshida, M., et al., "GM-CSF Regulates Protein and Lipid Catabolism by Alveolar Macrophages", Am J Physiol Lung Cell Mol Physiol, 2001, 280:L379-386, 8 pgs.

* cited by examiner

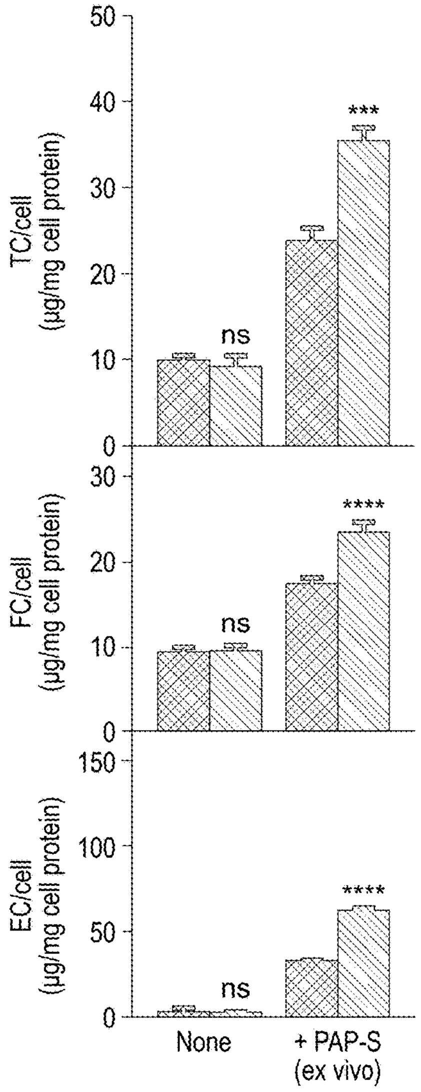
FIG. 1G
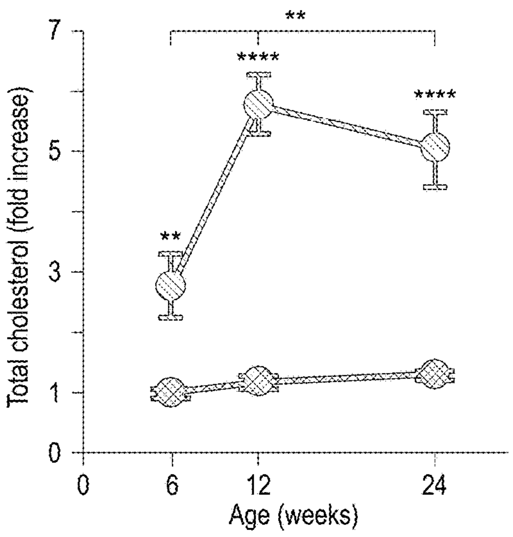
FIG. 1H
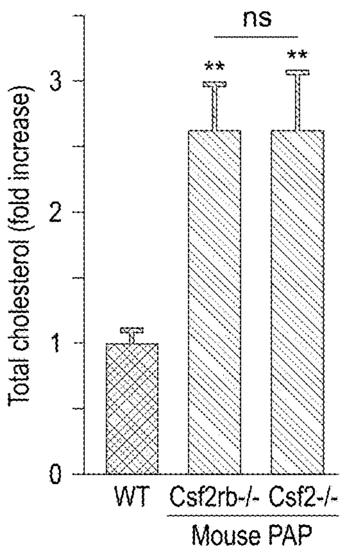
FIG. 1I

BAL Turbidity (OD 600 nm)
P=.057

BAL Turbidity (OD 600 nm)
***
****
nd

SatPC in BAL (μmoles/ml BAL)
*

SatPC in BAL (μmoles/mouse)
***
****
nd

Cholesterol In BAL (mg/ml)
**
C
PAP

Cholesterol in BAL (mg/mouse)
**
***
****
nd
Age (weeks)

Human control
Human PAP
Mouse WT
Mouse PAP

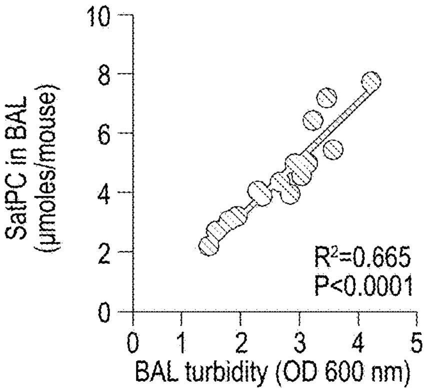
FIG. 2G
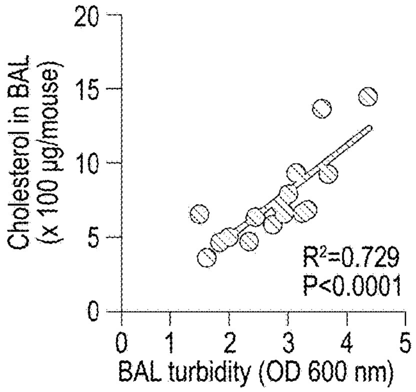
FIG. 2H
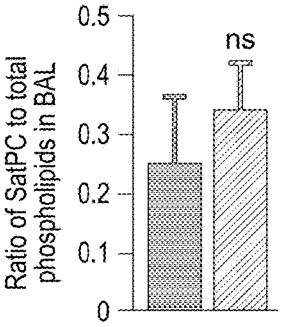
FIG. 2I
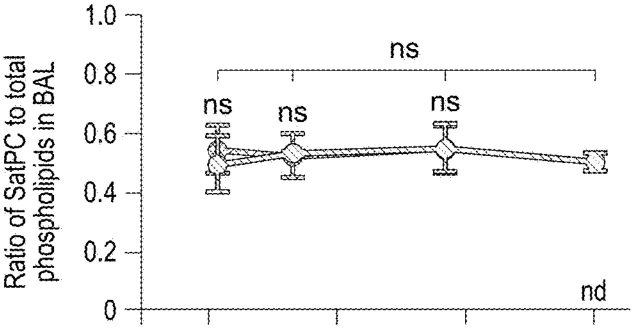
FIG. 2J

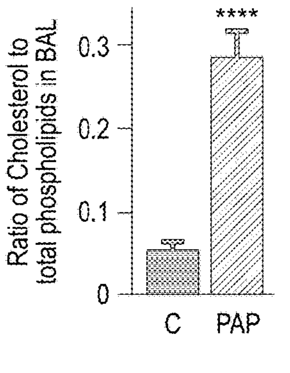
FIG. 2K
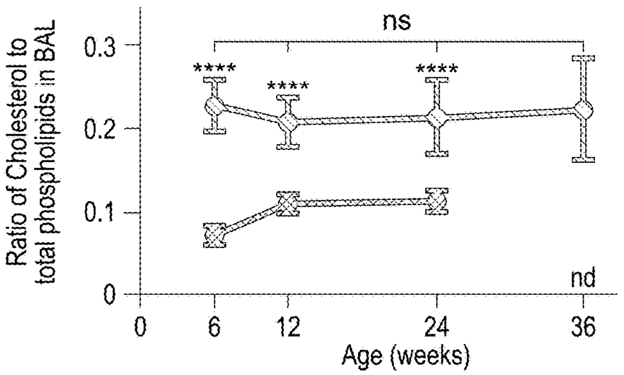
FIG. 2L
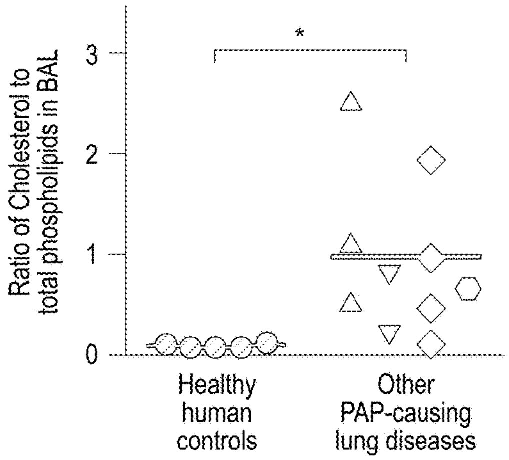
FIG. 2M
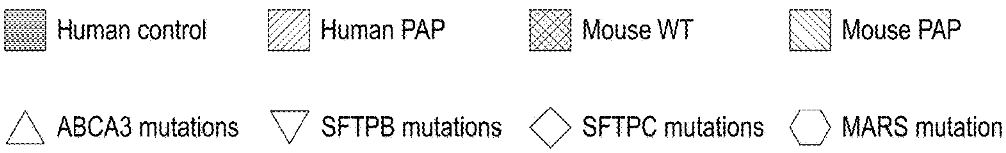

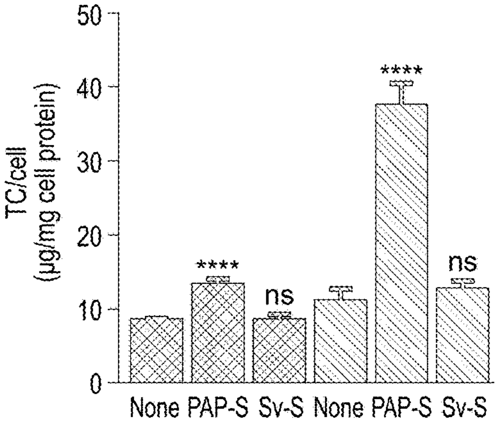
FIG. 3A
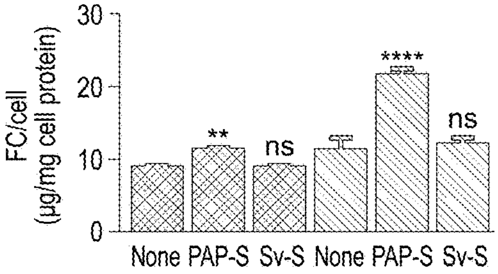
FIG. 3B
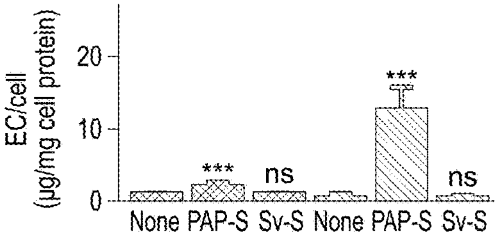
FIG. 3C
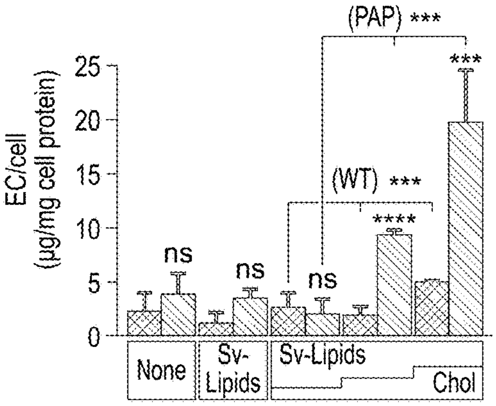
FIG. 3D

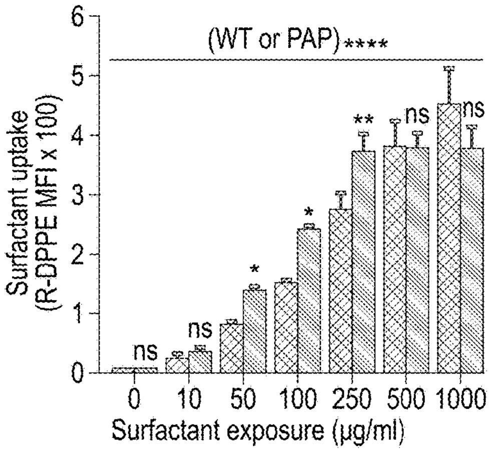
FIG. 3E
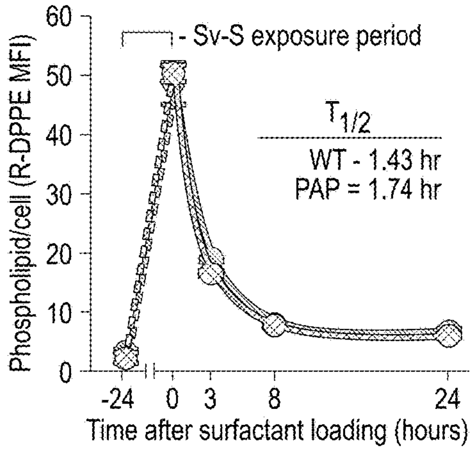
FIG. 3F
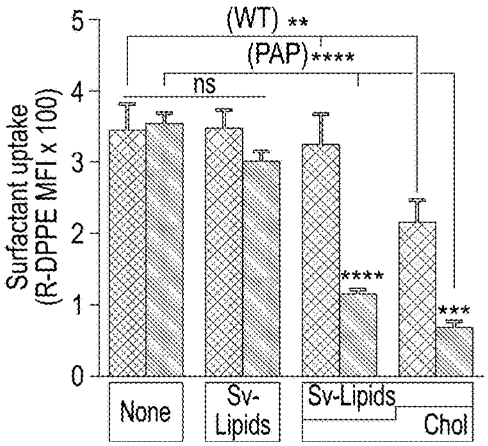
FIG. 3G
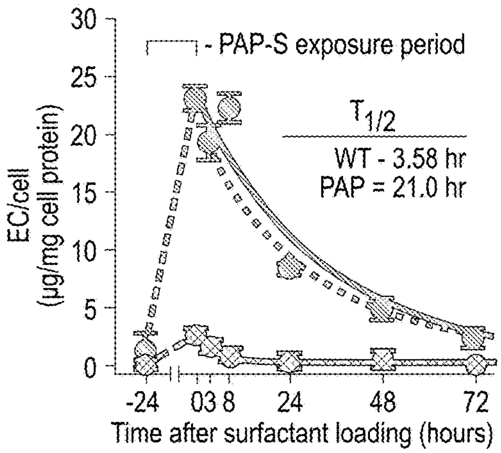
FIG. 3H

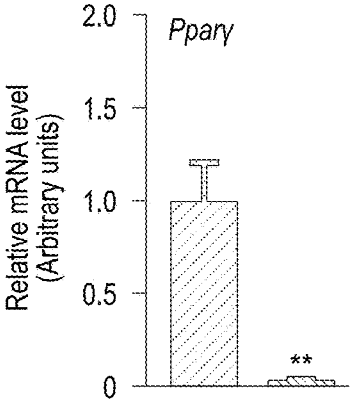
FIG. 4A
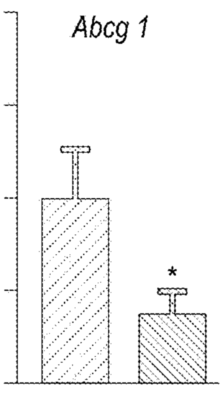
FIG. 4B
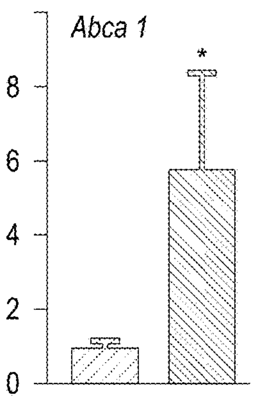
FIG. 4C
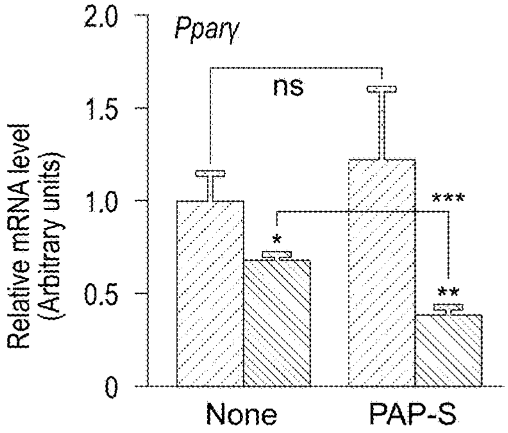
FIG. 4D
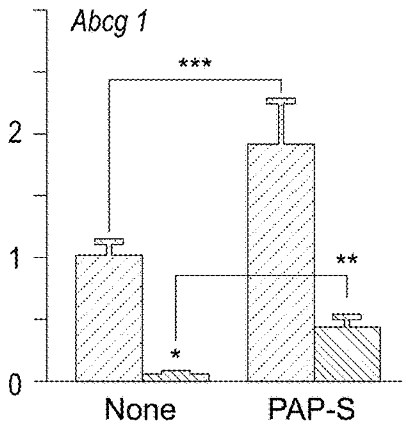
FIG. 4E

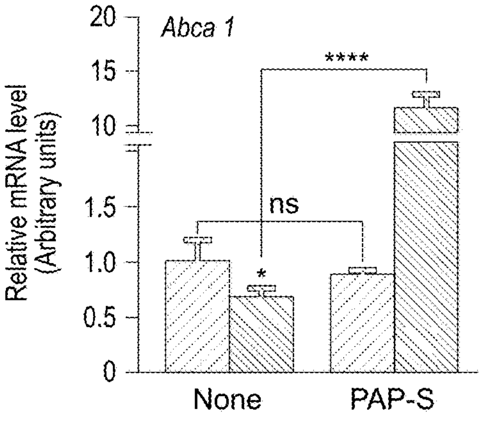
FIG. 4F
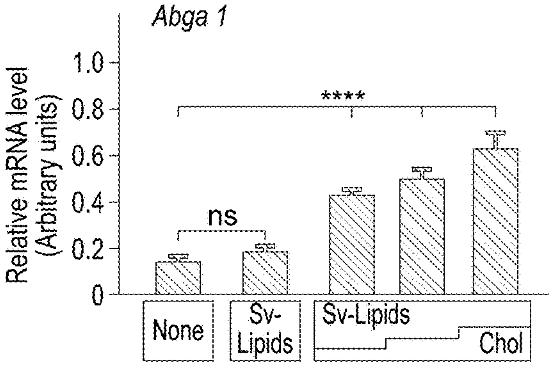
FIG. 4G
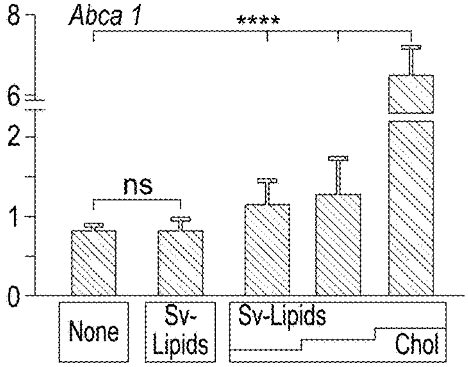
FIG. 4H

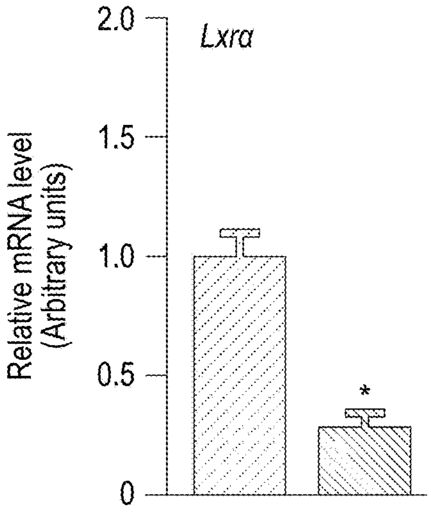
FIG. 7A
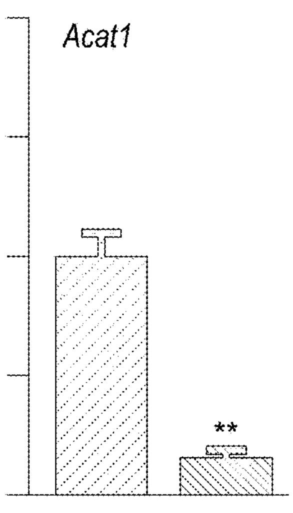
FIG. 7B
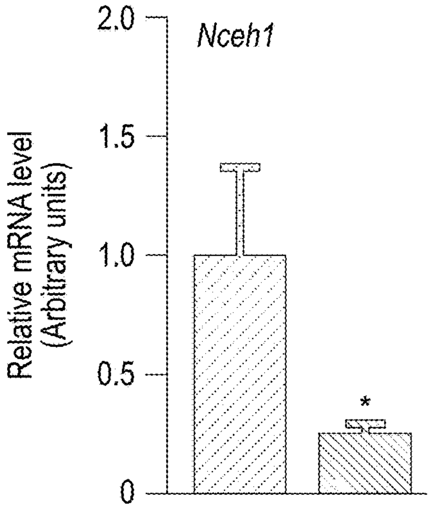
FIG. 7C
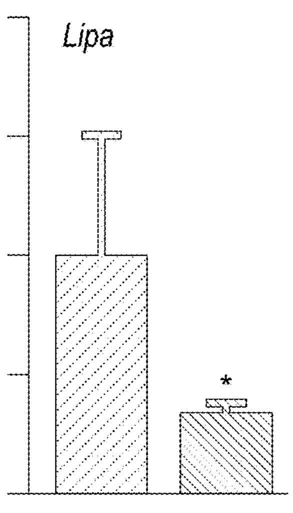
FIG. 7D

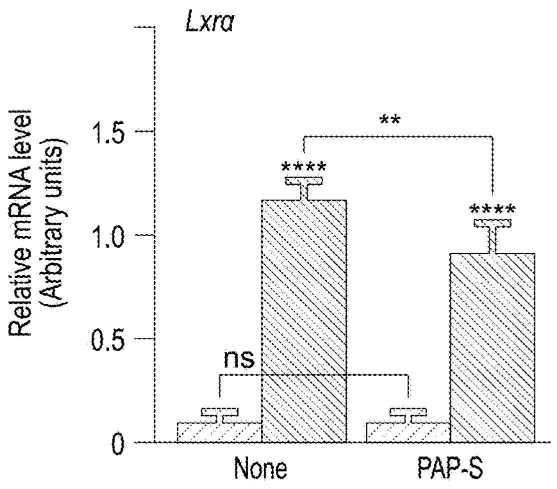
FIG. 7E
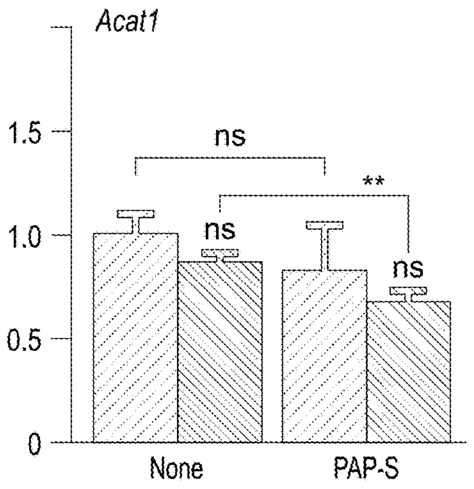
FIG. 7F
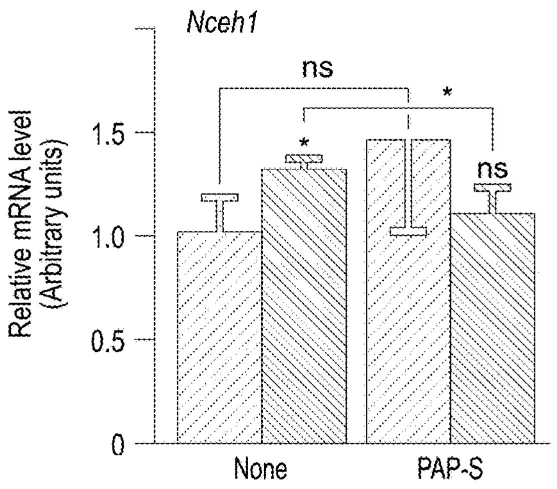
FIG. 7G
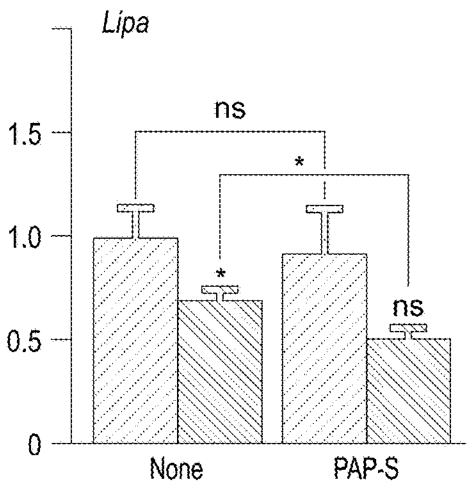
FIG. 7H

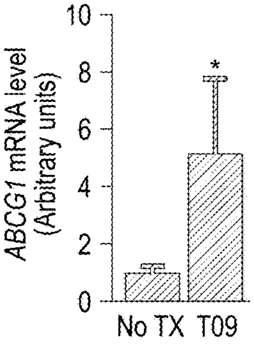
FIG. 8A
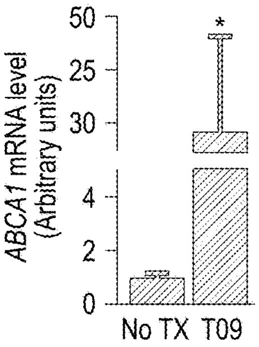
FIG. 8B
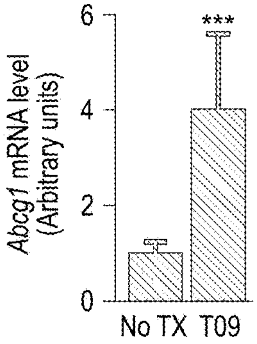
FIG. 8C
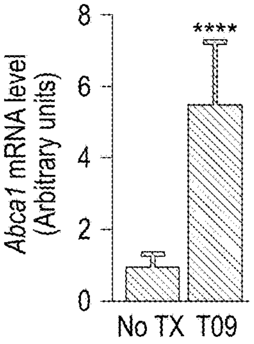
FIG. 8D
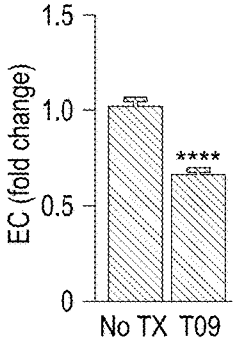
FIG. 8E
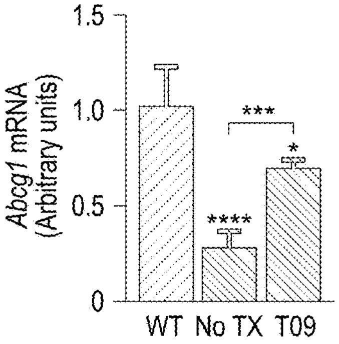
FIG. 8F
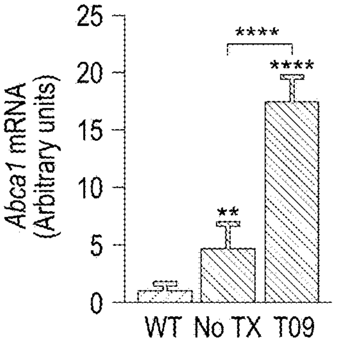
FIG. 8G

COMPOSITION AND METHODS FOR TREATMENT OF LUNG DISORDERS CHARACTERIZED BY CHOLESTEROL DYSREGULATION

CROSS REFERENCE TO RELATED APPLICATIONS

This application claims priority to and the benefit of U.S. Ser. No. 62/321,892, entitled "Treatment for Autoimmune Pulmonary Alveolar Proteinosis (PAP)," filed Apr. 13, 2016, the contents of which are incorporated in their entirety for all purposes.

GOVERNMENT SUPPORT CLAUSE

This invention was made with government support under HL085453 awarded the National Institutes of Health. The government has certain rights in the invention.

BACKGROUND

Autoimmune PAP is a serious, rare, and chronic debilitating pulmonary disease characterized by alveolar surfactant accumulation which results in hypoxemic respiratory failure, and innate immune deficiency. PAP syndrome occurs in a group of heterogenous diseases that affect men, women, children, and neonates, including individuals of all ethnicities and geographic locations. PAP affects fewer than 50,000 people worldwide (estimated 2100 US) for which whole lung lavage (WLL) is the standard of care. Whole lung lavage is an invasive treatment that is not widely available, is inefficient and associated with morbidity from general anesthesia, tracheal abrasion caused by prolonged intubation with a double lumen endotracheal tube, mechanical ventilation, and repeated filling and draining of the lung with saline while percussing the chest to emulsify surfactant lipids into the saline. Further, the procedure requires an expert bronchoscopist to perform the procedure. This procedure is invasive and more complicated and difficult in children, and is unavailable at most medical centers. Currently, there is no FDA-approved disease modifying treatment. Thus, there is a significant, unmet need for easily accessible, affordable oral drug therapy for autoimmune PAP.

BRIEF SUMMARY

Disclosed are compositions and methods for treating a condition characterized by a dysregulation in macrophage lipid homeostasis. The disclosed methods may include the administration of an agent selected from a PPARγ agonist, a LXR agonist, or a combination thereof. In certain aspects, the disclosed methods may be used to prevent, treat, or ameliorate a condition such as pulmonary alveolar proteinosis (PAP) and/or symptoms associated therewith.

BRIEF DESCRIPTION OF THE DRAWINGS

FIGS. 1A-1I. Cholesterol accumulation in surfactant-exposed macrophages. FIG. 1A, Alveolar macrophages from hereditary or autoimmune PAP patients (hPAP or aPAP), human controls, a non-human primate injected with GMAb (NHP-GMAb), or 6 week-old WT or PAP mice (Csf2−/−, or Csf2rb−/−) after Diff-Quick (DQ) or oil-red-O (ORO) staining and light microscopy (20×) or uranyl acetate staining and electron microscopy (EM). FIGS. 1B-1C, TLC/primuline staining of alveolar macrophage total lipid extracts. Markers: esterified cholesterol (EC), triglycerides (TG), free cholesterol (FC), fatty acids (FA), phosphatidylcholine (PC), origin (O). FIGS. 1D-1I, Levels of total, free, and esterified cholesterol (TC, FC, EC) from the indicated alveolar (FIGS. 1D, 1E, 1H, 1I), BMD (FIG. 1F), or peritoneal (FIG. 1G) macrophages without/with surfactant exposure as indicated. Data are mean ±SD of 3 humans (FIG. 1D) or 3-4 mice (FIGS. 1E-1I) per group. $*P<0.05$, $p<0.01$, $*P<0.001$, $****P<0.0001$, not significant (ns).

FIGS. 2A-2M. Changes in surfactant lipid composition in PAP. FIGS. 2A-2B, Bronchoalveolar lavage (BAL) turbidity (optical density (OD) at λ=600 nm). FIGS. 2C-2L, Composition of total lipid extracts from BAL obtained from humans (FIGS. 2C-2K, FIG. 2M) and mice (FIGS. 2D-2L) as indicated. Data are mean ±SD of 5 (human) or 4 (mice) individuals/group or time-point. $*P<0.05$, $P<0.01$, $*P<0.001$, $****P<0.0001$. Not done (nd).

FIGS. 3A-3N. Cholesterol drives lipid accumulation in PAP macrophages. FIGS. 3A-3D, TC, FC, EC levels in BMD macrophages without or after exposure to PAP-S, Sv-S, Sv-S Lipids, or Sv-S Lipids supplemented with cholesterol 10%, 25%, or 50% (wt/wt) (Sv-Lipids/Chol) evaluated as described above (FIGS. 1F-1G). FIGS. 3E-3F, Uptake (FIG. 3E) and clearance (FIG. 3F) of Sv-S spiked with rhodamine-conjugated dipalmitoylphosphatidyl-ethanolamine (R-DPPE) by BMD macrophages determined by flow cytometry. FIG. 3G, Uptake of R-DPPE-spiked Sv-S by BMD macrophages without (None) or 24 hours after exposure to Sv-Lipids or Sv-Lipids supplemented with 25% or 50% free cholesterol (wt/wt) (Sv-Lipids/Chol) determined by flow cytometry. FIG. 3H, Cholesterol clearance kinetics after pulse exposure to PAP-S for 24 hours, cell washing, and measurement of EC/cell. FIGS. 3K-3N, Kinetics/dynamics of GM-CSF-regulated cholesterol clearance. FIG. 3K, schematic showing times BMD macrophages were exposed to M-CSF/GM-CSF and taken to initiate exposure to PAP-S (arrows) and measurement of EC accumulation as described in Methods. Loss (FIG. 3L), restoration (FIG 3M), and concentration-dependent stimulation (FIG. 3N) of cholesterol clearance by GM-CSF. Data are mean±SD of 3 determinations/condition. $*P<0.05$, $P<0.01$, $*P<0.001$, $****P<0.0001$.

FIGS. 4A-4H. Expression of cholesterol transporter genes in PAP macrophages. FIGS. 4A-4C, mRNA levels in primary alveolar macrophages from the indicated mice determined by RT-PCR. FIGS. 4D-4H, mRNA levels in cultured BMD macrophages (measured by RT-BCR) without or 24 hours after exposure to PAP-S (FIGS. 4D-4F) or cholesterol-free Survanta lipid extract (Sv-Lipids) or Sv-Lipids supplemented with cholesterol to 10%, 25% or 50% (wt/wt) as indicated by yellow/purple bars (Sv-Lipids/Chol) (FIGS. 4G-4H). Data are mean±SD (3 separate determinations/condition). $*P<0.05$, $P<0.01$, $*P<0.001$, $****P<0.0001$.

FIGS. 5A-5E, In vitro studies. FIGS. 5A-5D, mRNA levels in the indicated primary human alveolar (FIGS. 5A-5B) or cultured mouse BMD (FIGS. 5C-5D) macrophages after incubation for 24 hours without (No Tx) or with pioglitazone (Pio) determined by RT-PCR. FIG. 5E, Accumulation of EC in BMD macrophages after incubation for 24 hours without (No Tx) or with pioglitazone (Pio)

followed by incubation for 24 hours to PAP-S. FIGS. 5F-5I, In vivo studies. mRNA levels in primary alveolar macrophages (FIGS. 5F-5G), BAL turbidity, (FIG. 5H), and BAL cholesterol levels (FIG. 5I) in PAP mice receiving low dose pioglitazone (Pio) for six weeks, or in age-matched, untreated WT or PAP mice (No Tx). Data are mean±SD for 8 mice/group. *P<0.05, P<0.01, *P<0.001, ****P<0.0001.

FIGS. 7A-7H. Expression of Cholesterol Regulatory Genes in PAP macrophages. FIGS. 7A-7D, Relative levels of mRNA for Lxrα (FIG. 7A) Acat1 (FIG. 7B), Nceh1 (FIG. 7C) and Lipa (FIG. 7D) in alveolar macrophages of WT and PAP mice measured by quantitative real time polymerase chain reaction (qRT-PCR) analysis. FIGS. 7E-7H, BMD macrophages from WT or PAP mice were exposed to PAP-S. After 24 hours, cellular mRNA levels of Lxrα (FIG. 7E) Acat1 (FIG. 7F), Nceh1 (FIG. 7G) and Lipa (FIG. 7H) were measured by RT-PCR analysis. Data represent the mean±SD of 3 separate determinations per condition. *P<0.05, P<0.01, *P<0.001, ****P<0.0001.

FIGS. 8A-8G. Therapeutic correction of cholesterol homeostasis in PAP Macrophages via the LXR pathway. FIGS. 8A-8E, In vitro T0901317 (T09) studies. Relative levels of mRNA for ABCG1 (FIG. 8A) and ABCA1 (FIG. 8B) in human PAP patient alveolar macrophages and levels of Abcg1 (FIG. 8C) or Abca1 (FIG. 8D) mRNA in BMD macrophages from PAP mice after culture for 24 hours with T09, FIG. 8E, BMD macrophages from PAP mice cultured for 24 hours with T09 or without T09 were then exposed to PAP-S for 24 hours and the amount of esterified cholesterol per cell was measured. FIGS. 8F-8G. In vivo T0901317 study. T09 was administered by oral gavage once daily for 7 days at a dose of 10 mg/kg/BW/Day to PAP mice. Relative levels of mRNA for Abca1 (FIG. 8F) or Abcg1 (FIG. 8G) in alveolar macrophages from PAP mice after oral T09 or from untreated, age-matched WT or PAP mice. Data are mean±SD of results for 8 mice per condition, and all data is expressed as treatment condition compared to control levels. *P<0.05, P<0.01, *P<0.001, ****P<0.0001.

DETAILED DESCRIPTION

Figure 1A:
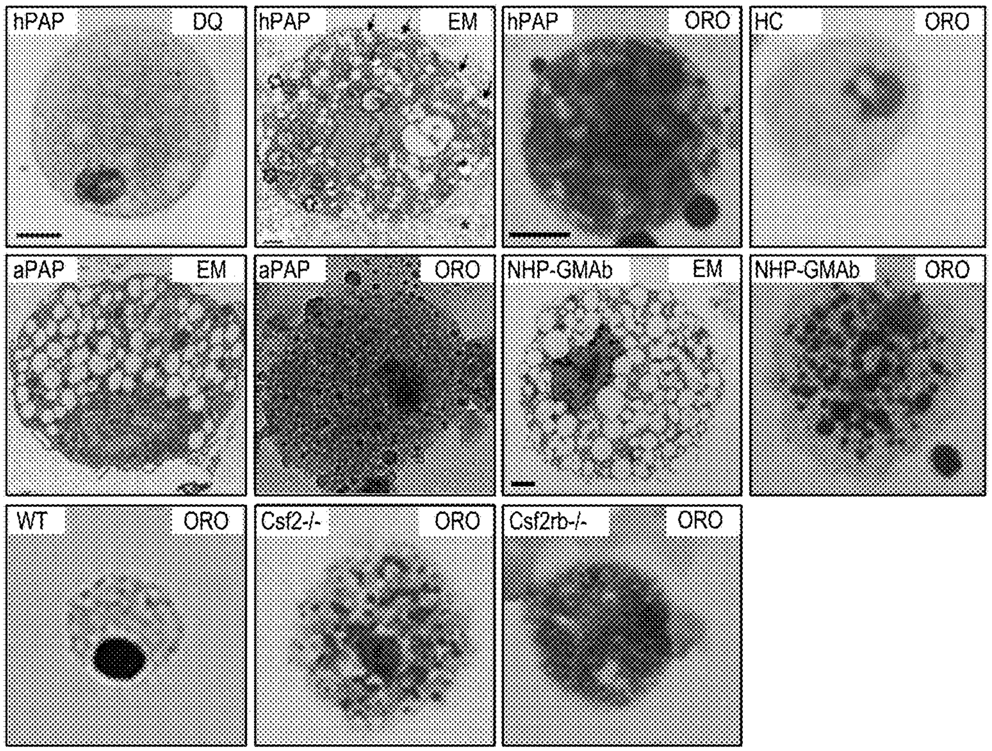

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms and expressions used herein have the ordinary meaning as is accorded to such terms and expressions with respect to their corresponding respective areas of inquiry and study except where specific meanings have otherwise been set forth herein.

As used herein and in the appended claims, the singular forms “a,” “and,” and “the” include plural referents unless the context clearly dictates otherwise. Thus, for example, reference to “a method” includes a plurality of such methods and reference to “a dose” includes reference to one or more doses and equivalents thereof known to those skilled in the art, and so forth.

The term “about” or “approximately” means within an acceptable error range for the particular value as determined by one of ordinary skill in the art, which will depend in part on how the value is measured or determined, e.g., the limitations of the measurement system. For example, “about” can mean within 1 or more than 1 standard deviation, per the practice in the art. Alternatively, “about” can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term “about” meaning within an acceptable error range for the particular value should be assumed.

The terms “individual,” “host,” “subject,” and “patient” are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

“Therapeutically effective amount” relates to the amount or dose of an active compound or composition described herein that will lead to one or more therapeutic effect, in particular, desired beneficial effects. A therapeutically effective amount of a substance can vary according to factors such as the disease state, age, sex, and weight of the subject, and the ability of the substance to elicit a desired response in the subject. Dosage regime may be adjusted to provide the optimum therapeutic response. For example, several divided doses may be administered daily or the dose may be proportionally reduced as indicated by the exigencies of the therapeutic situation.

The phrase “pharmaceutically acceptable,” as used in connection with compositions of the disclosure, refers to molecular entities and other ingredients of such compositions that are physiologically tolerable and do not typically produce untoward reactions when administered to a subject (e.g., human). In certain embodiments, as used herein, the term “pharmaceutically acceptable” means approved by a regulatory agency of a Federal or a state government or listed in the U.S. Pharmacopeia or other generally recognized pharmacopeia for use in mammals (e.g., humans).

The term “carrier” applied to pharmaceutical compositions of the disclosure refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable, or synthetic origin, such as peanut oil, soybean oil, mineral oil, sesame oil and the like. Suitable pharmaceutical carriers are known in the art and described, for example, in “Remington’s Pharmaceutical Sciences” by E. W. Martin, 18th Edition.

Macrophages are critical to organ structure and function in health and disease. Applicant has identified several novel therapeutic targets for pharmacotherapeutic development.

Applicants have found that the primary molecular/cellular abnormality in autoimmune PAP is the disruption of GM-CSF-dependent cholesterol clearance by alveolar macrophages by neutralizing antibodies directed to GM-CSF. The loss of GM-CSF signalling results in reduced PU.1/CEBP-mediated PPAR expression/activation. This, in turn, reduces the kinetics of cholesterol clearance, resulting in the cellular response of esterification and storage of cholesterol in lipid droplets that fill the cell, impair intracellular transport, and secondarily reduce the clearance of surfactant phospholipids and result in surfactant accumulation in alveoli, eventually leading to hypoxemic respiratory failure.

Alveolar macrophages isolated from patients with autoimmune PAP, as well as studies in GM-CSF deficient mice, show that exposure to the PPAR ligand, pioglitazone, increases PPAR-mediated expression of critical downstream targets (e.g., ABCG1, downstream of GM-CSF). Applicant has found that pioglitazone therapy of GM-CSF deficient mice reduced the severity of PAP lung disease, establishing the feasibility of this therapeutic approach as a therapy for autoimmune PAP (and hereditary PAP due to GM-CSF receptor defects).

Disclosed are methods of treating a condition characterized by a dysregulation in macrophage lipid homeostasis. The method may comprise the step of administering an agent selected from a PPARγ agonist, a LXR agonist, or a combination thereof.

In one aspect, the condition to be treated may be selected from hereditary pulmonary alveolar proteinosis (PAP), autoimmune pulmonary alveolar proteinosis (PAP), congenital PAP caused by a mutation in a gene selected from a gene encoding surfactant protein B, a gene surfactant protein C, a gene encoding Thyroid transcription factor 1 (aka NKX2.1), or a gene encoding ABCA3, secondary PAP caused by disruption of alveolar macrophage surfactant clearance function and/or alveolar macrophage numbers (for example, which may be caused by inhalation of toxic inorganic dusts such as silica, aluminum, or titanium), a surfactant-related lung disease, or diseases associated with macrophage foam-cell formation (for example, atherosclerosis resulting in cardiovascular disease such as myocardial infarction and cerebrovascular disease including stroke).

In one aspect, the PPARγ agonist may be pioglitazone. Pioglitazone is a thiazolidinedione that selectively stimulates the nuclear receptor peroxisome proliferator-activated receptor gamma (PPAR-γ) and to a lesser extent PPAR-α. Pioglitazone is available under the brand name ACTOS, and is available from Takeda Pharmaceuticals. Pioglitazone has the following structure:

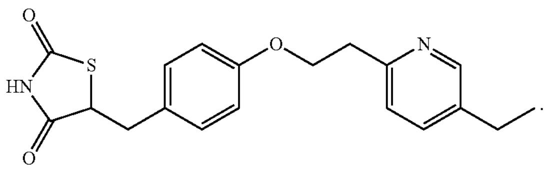 [SMILES: CCc1ccc(CCOc2ccc(CC3SC(=O)NC3=O)cc2)nc1]

Pharmaceutically acceptable salts thereof are further within the scope of the disclosure. The PPARγ receptor is described in Chandra, et al, "Structure of the intact PPAR-γ-RXR-α-nuclear receptor complex on DNA," Nature 456 (7220): 350-356; 2008, incorporated by reference.

In one aspect, the LXR (Liver X Receptors (LXRα and LXRβ)) agonist may be T0901317 (N-(2,2,2-trifluoroethyl)-N-[4-[2,2,2-trifluoro-1-hydroxy-1-(trifluoromethyl)ethyl]phenyl]-benzenesulfonamide), having the structure

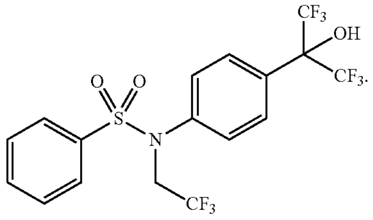 [SMILES: O=S(=O)(c1ccccc1)N(CC(F)(F)F)c1ccc(C(O)(C(F)(F)F)C(F)(F)F)cc1]

T0901317 is a potent and selective agonist for both LXRα and LXRβ, and is available from Cayman Chemical. The LXR receptor is described in Willy et al, "LXR, a nuclear receptor that defines a distinct retinoid response pathway," Genes Dev. 9: 1033-45; 1995, incorporated by reference.

In one aspect, the PPARγ and/or LXR agonist may be administered orally.

In one aspect, the PPARγ and/or LXR agonist may be administered via inhalation.

In one aspect, the PPARγ and/or LXR agonist may be administered in an amount sufficient to reduce cholesterol in alveolar macrophages.

In one aspect, the PPARγ and/or LXR agonist may be administered in an amount sufficient to increase cholesterol clearance in alveolar macrophages.

A method of decreasing lung infection in an individual having PAP is further disclosed. In this aspect, the method may comprise the step of administering an agent selected from a PPARγ agonist, an LXR agonist, and a combination thereof.

In one aspect, a kit or article of manufacture is disclosed. In this aspect, the kit or article of manufacture may comprise a container, a composition comprising a PPARγ agonist, a LXR agonist, or a combination thereof, and instructions for administering said active agent to an individual diagnosed or suspected of having PAP or a symptom associated with PAP. The container may contain a predetermined volume of the agent/active ingredient, and may be, in some aspects, a unit dose. In one aspect, the container may contain a dose of pioglitazone, or pharmaceutically acceptable salt thereof, wherein the dose is a unit dose having a dosage weight of 15 mg, 30 mg, or 45 mg. The kit or article of manufacture may further contain instructions or a dosing device associated with the container. The dosage form may be an oral dosage form, or may be a form suitable for bronchial administration, wherein said bronchial administration is via inhalation.

Dosage

As will be apparent to those skilled in the art, dosages outside of these disclosed ranges may be administered in some cases. Further, it is noted that the ordinary skilled clinician or treating physician will know how and when to interrupt, adjust, or terminate therapy in consideration of individual patient response.

In certain embodiment, the dosage of an agent disclosed herein, based on weight of the active compound, administered to prevent, treat, manage, or ameliorate one or more symptoms of the disclosed disorder in a subject may be about 0.25 mg/kg, 0.5 mg/kg, 0.1 mg/kg, 1 mg/kg, 2 mg/kg, 3 mg/kg, 4 mg/kg, 5 mg/kg, 6 mg/kg, or more of a subject's body weight. In another embodiment, the dosage of an agent disclosed herein to prevent, treat, manage, or ameliorate one or more symptoms of the disclosed disorder in a subject is a unit dose of about 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In one aspect, an agent disclosed herein may be present in an amount of from about 0.5% to about 95%, or from about 1% to about 90%, or from about 2% to about 85%, or from about 3% to about 80%, or from about 4%, about 75%, or from about 5% to about 70%, or from about 6%, about 65%, or from about 7% to about 60%, or from about 8% to about 55%, or from about 9% to about 50%, or from about 10% to about 40%, by weight of the composition.

The compositions may be administered in oral dosage forms such as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular forms all utilizing dosage forms well known to those of ordinary skill in the pharmaceutical arts. The compositions may be administered by intranasal route via topical use of suitable intranasal vehicles, or via a transdermal route, for example using conventional transdermal skin patches. A dosage protocol for administration using a transdermal delivery system may be continuous rather than intermittent throughout the dosage regimen.

The pharmaceutical compositions may include suitable dosage forms for oral, parenteral (including subcutaneous, intramuscular, intradermal and intravenous), transdermal, sublingual, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. Oral preparations include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. For topical or nasal administration, penetrants or permeation agents that are appropriate to the particular barrier to be permeated are used in the formulation. Such penetrants are generally known in the art. The compositions may take the form suited for inhalation. Methods of manufacturing such compositions will be understood by one of ordinary skill in the art. The pharmaceutical compositions are prepared by conventional techniques appropriate to the desired preparation containing appropriate amounts of the active ingredient, that is, one or more of the disclosed active agents or a pharmaceutically acceptable salt thereof according to the invention.

The dosage of an agent disclosed herein used to achieve a therapeutic effect will depend not only on such factors as the age, weight and sex of the patient and mode of administration, but also on the degree of inhibition desired and the potency of an agent disclosed herein for the particular disorder or disease concerned. It is also contemplated that the treatment and dosage of an agent disclosed herein may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

Kits

Kits are also provided. In one aspect, a kit may comprise or consist essentially of agents or compositions described herein. The kit may be a package that houses a container which may contain a disclosed active or pharmaceutically acceptable salt thereof as disclosed herein, and also houses instructions for administering the agent or composition to a subject. In one aspect, a pharmaceutical pack or kit is provided comprising one or more containers filled with one or more composition as disclosed herein. Associated with such container(s) can be various written materials such as instructions for use, or a notice in the form prescribed by a governmental agency regulating the manufacture, use or sale of pharmaceuticals or biological products, which notice reflects approval by the agency of manufacture, use, or sale for human administration.

As there may be advantages to mixing a component of a composition described herein and a pharmaceutically acceptable carrier, excipient or vehicle near the time of use, kits in which components of the compositions are packaged separately are disclosed. For example, the kit can contain an active ingredient in a powdered or other dry form in, for example, a sterile vial or ampule and, in a separate container within the kit, a carrier, excipient, or vehicle, or a component of a carrier, excipient, or vehicle (in liquid or dry form). In one aspect, the kit can contain a component in a dry form, typically as a powder, often in a lyophilized form in, for example, a sterile vial or ampule and, in a separate container within the kit, a carrier, excipient, or vehicle, or a component of a carrier, excipient, or vehicle. Alternatively, the kit may contain a component in the form of a concentrated solution that is diluted prior to administration. Any of the components described herein, any of the carriers, excipients or vehicles described herein, and any combination of components and carriers, excipients or vehicles can be included in a kit.

Optionally, a kit may also contain instructions for preparation or use (e.g., written instructions printed on the outer container or on a leaflet placed therein) and one or more devices to aid the preparation of the solution and/or its administration to a patient (e.g., one or a plurality of syringes, needles, filters, tape, tubing (e.g., tubing to facilitate intravenous administration) alcohol swabs and/or the Band-Aid® applicator). Compositions which are more concentrated than those administered to a subject can be prepared. Accordingly, such compositions can be included in the kits with, optionally, suitable materials (e.g., water, saline, or other physiologically acceptable solutions) for dilution. Instructions included with the kit can include, where appropriate, instructions for dilution.

In other embodiments, the kits can include pre-mixed compositions and instructions for solubilizing any precipitate that may have formed during shipping or storage. Kits containing solutions of a disclosed active, or a pharmaceutically acceptable salt thereof, and one or more carriers, excipients or vehicles may also contain any of the materials mentioned above (e.g., any device to aid in preparing the composition for administration or in the administration per se). The instructions in these kits may describe suitable indications (e.g., a description of patients amenable to treatment) and instructions for administering the solution to a patient.

EXAMPLES

To determine mechanisms by which granulocyte/macrophage-colony stimulating factor (GM-CSF) signaling normally maintains surfactant homeostasis and how its disruption causes pulmonary alveolar proteinosis (PAP), Applicant evaluated the lipid composition in alveolar macrophages and lung surfactant in humans and mice, macrophage-mediated surfactant clearance kinetics/dynamics, and cholesterol-targeted pharmacotherapy of PAP in vitro and in vivo.

Applicant found that, without GM-CSF signaling, surfactant-exposed macrophages massively accumulated cholesterol ester-rich lipid-droplets and surfactant had an increased proportion of cholesterol. GM-CSF regulated cholesterol clearance in macrophages in constitutive, dose-dependent, and reversible fashion but did not affect phospholipid clearance. Applicant found that PPARγ-agonist therapy increased cholesterol clearance in macrophages and reduced disease severity in PAP mice. Without intending to be limited by theory, it is believed that GM-CSF is required for cholesterol clearance in macrophages, and that reduced cholesterol clearance may be the primary macrophage defect driving PAP pathogenesis. This further supports the feasibility of the use of pioglitazone as a novel pharmacotherapy of PAP.

GM-CSF has emerged as an important regulator of the ontogeny, renewal, and functions of macrophages in health and disease, particularly in the lung[1-4]. For example, pulmonary alveolar macrophages require GM-CSF to maintain surfactant homeostasis, which is critical to alveolar stability and lung function[5,6], and disruption of GM-CSF signaling causes pulmonary alveolar proteinosis (PAP)—a syndrome of progressive alveolar surfactant accumulation and resulting hypoxemic respiratory failure that occurs in men, women and children[3,7]. In humans, PAP is caused by neutralizing GM-CSF autoantibodies[8,9] or mutations in CSF2RA[10,11] or CSF2RB[12,11] encoding GM-CSF receptor α and β, respectively. In non-human primates, PAP is recapitulated by administration of patient-derived GM-CSF autoantibodies[7,9]. In mice, PAP develops after gene ablation of Csf2[5,6] or Csf2rb[14]. In each, the lung disease is histologically, biochemically, and physiologically similar and driven by disruption of GM-CSF signaling, which alveolar macrophages require to clear surfactant normally[15]. However, the mechanism responsible is not known.

Surfactant is composed of 80% polar lipids (primarily saturated phosphatidylcholine (SatPC) and other less-abundant phospholipids), 10% neutral lipids (primarily free cholesterol with small amounts of triglycerides and free fatty acids), and 10% proteins[16,17]. Cholesterol content regulates surfactant fluidity and function in lunged animals and can change rapidly, especially under extremes of temperature[18]. Surfactant homeostasis is maintained by balanced secretion by alveolar epithelial type II cells and clearance via recycling and catabolism in these cells and catabolism in alveolar macrophages[19]. Reports that the relative composition of surfactant phospholipids is normal in PAP patients[20] and $Csf2^{-/-}$ mice[21,22] led to a widely-held belief that surfactant accumulation in PAP is caused by impaired catabolism of phospholipids in alveolar macrophages[15], however, no such mechanism has been found.

Applicant observed that, in PAP, alveolar macrophages have abnormal expression of PPARγ[23-25], ABCA1[25,26] and ABCG1[23], factors important in cholesterol transport in macrophages[26,] suggesting that disruption of cholesterol homeostasis rather than impaired surfactant phospholipid catabolism in macrophages may drive pathogenesis. Applicant addressed this hypothesis by first identifying the lipids accumulating within alveolar macrophages in PAP. Applicant also evaluated GM-CSF regulation of surfactant uptake and clearance by macrophages, and PPARγ - or LXR-agonist mediated pharmacologic correction of PAP-related abnormalities in human and murine macrophages in vitro, and in PAP mice in vivo.

Lipid Accumulation in PAP Macrophages

Figure 1B:
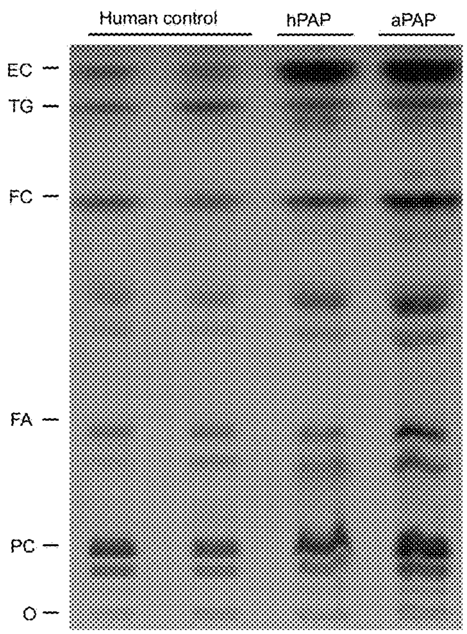
Figure 1C:
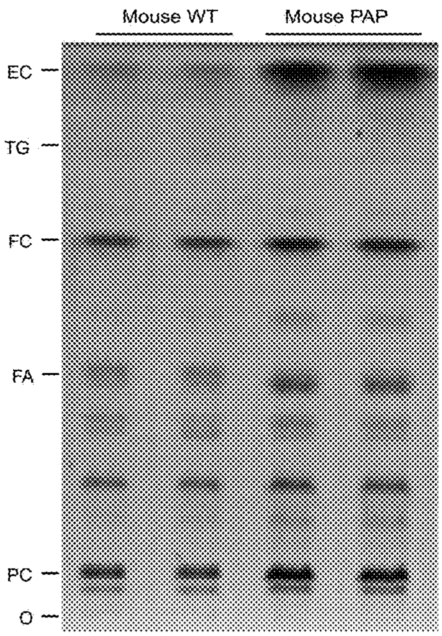
Figures 1D, 1E, 1F:
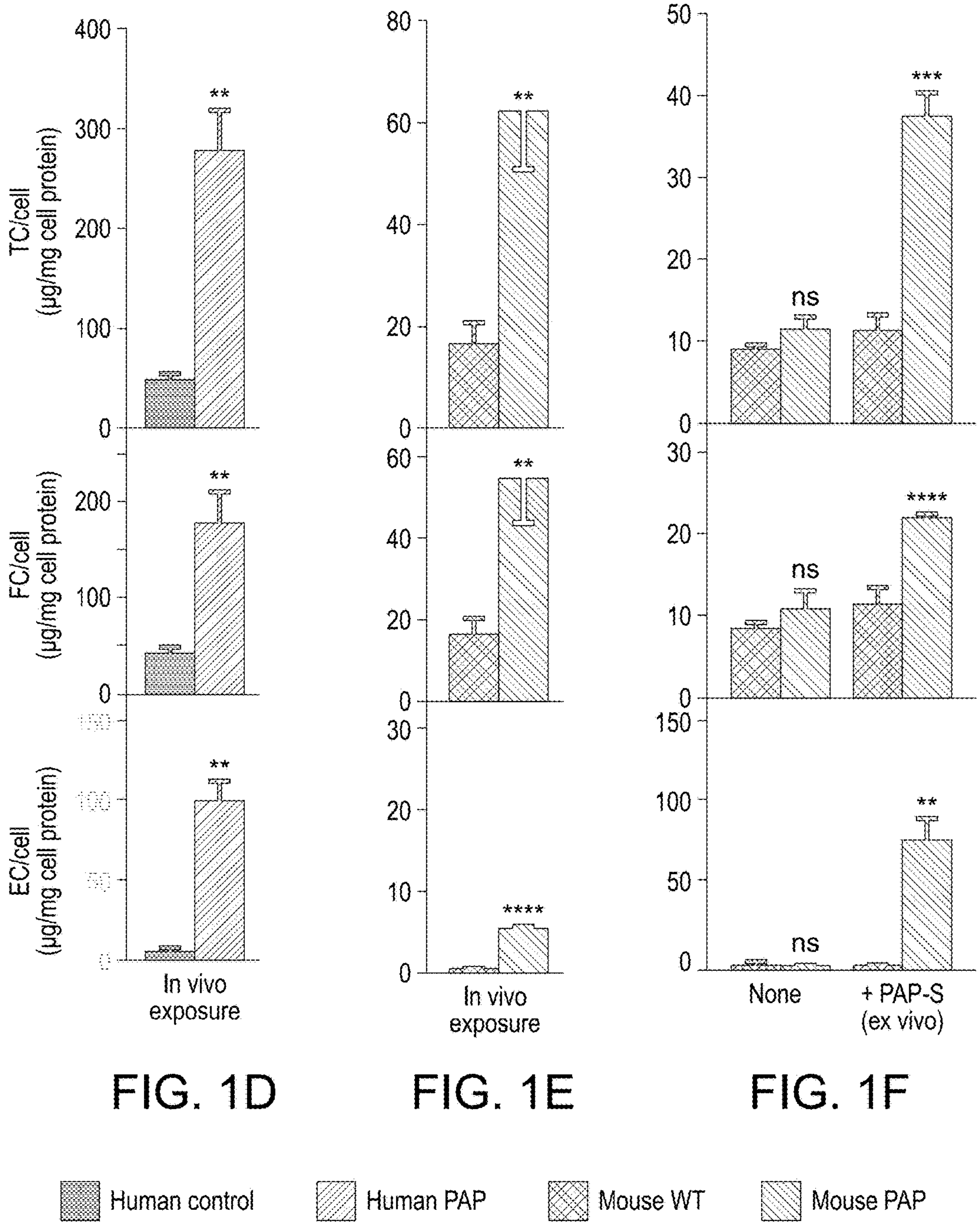

Applicant characterized the lipids accumulating in alveolar macrophages in PAP, as the earliest cellular abnormality following disruption of GM-CSF signaling is the development of foamy alveolar macrophages enlarged by accumulation of intracytoplasmic lipid droplets[9]. Alveolar macrophages from humans, primates, and mice with PAP stained positive with oil-red-O indicating the presence of neutral lipids; fatty acids, triglycerides or cholesterol ester[27,28] (FIG. 1A). Surfactant lipid composition was evaluated relative to total surfactant lipids rather than to the polar lipid fraction as prior studies had done[21] using a novel thin layer chromatography (TLC) method permitting simultaneous evaluation of polar and non-polar lipids. Compared to healthy controls, alveolar macrophages from PAP patients had increased levels of esterified and free cholesterol but no major changes in triglycerides or free fatty acids, and minimal changes in levels of phospholipid species (FIG. 1B). Similar results were seen in $Csf2^{-/-}$ mice compared to WT controls (FIG. 1C). Using a highly sensitive fluorometric method, Applicant found that, compared to corresponding healthy controls, total, free, and particularly esterified cholesterol levels were markedly increased in alveolar macrophages from PAP patients (FIG. 1D) and also from $Csf2^{-/-}$ mice (FIG. 1E).

To determine if this phenotype was specific to alveolar macrophages or common to other macrophage populations, similar studies were done with bone marrow derived (BMD) and peritoneal macrophages. Compared to WT controls, BMD macrophages from $Csf2^{-/-}$ mice had no increase in cholesterol levels at baseline but had marked increases in both free and esterified cholesterol after exposure to PAP patient-derived surfactant (PAP-surfactant) (FIG. 1F). Similar results were seen for peritoneal macrophages at baseline and after exposure to PAP-surfactant (FIG. 1G). Compared to age-matched WT controls, the cholesterol level in alveolar macrophages from $Csf2^{-/-}$ mice was increased 2.9-fold at six weeks, rose further to 5.4-fold at 12 weeks, plateaued at 5-fold at 24 weeks (FIG. 1H), and was similarly increased in $Csf2^{-/-}$ and $Csf2^{-/-}$ mice (FIG. 1I). These results indicate that esterified and free cholesterol are the predominant lipid species accumulating in alveolar macrophages in PAP, GM- CSF regulation of cholesterol clearance is not limited to alveolar macrophages but is common to other macrophage populations, and accumulation of cholesterol is not an intrinsic defect caused by GM-CSF deficiency but requires exposure to surfactant.

GM-CSF Regulates Surfactant Composition

Figures 2A, 2B, 2C, 2D, 2E, 2F:
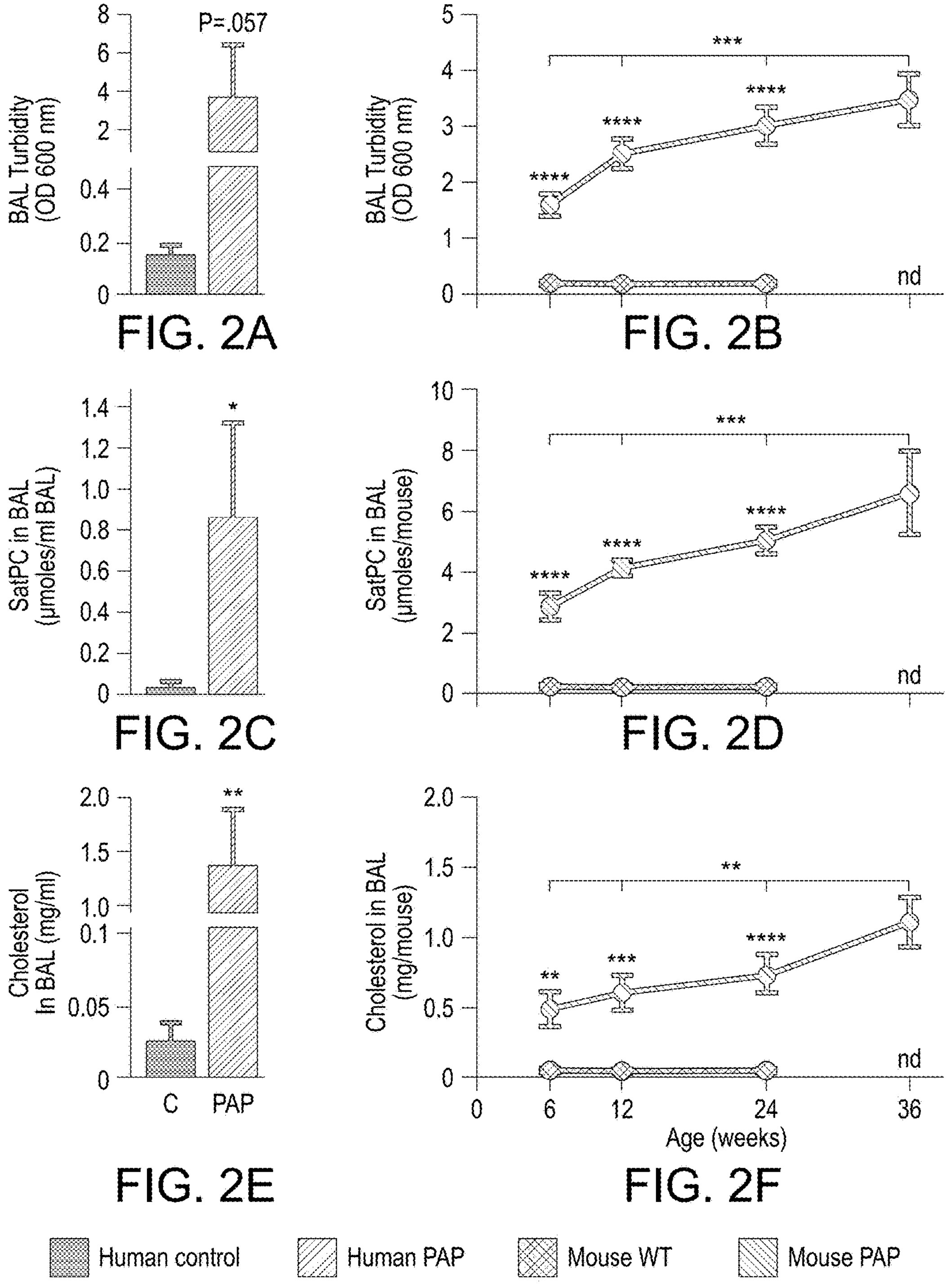

Applicant next sought to determine if disruption of GM-CSF signaling alters surfactant lipid composition or if surfactant lipid composition changes with disease progression as measured by bronchoalveolar lavage (BAL) turbidity, an excellent measure of global measure of surfactant accumulation[4]. BAL turbidity was increased in PAP patients compared to human controls (FIG. 2A) and increased with age in $Csf2^{-/-}$ mice while remaining low and constant in WT mice (FIG. 2B). Both SatPC and cholesterol in BAL were increased in surfactant from PAP patients compared to controls and Csf2−/− mice compared to WT mice (FIGS. 2C-2F). BAL turbidity correlated well with age-dependent, disease severity-related changes in both SatPC and cholesterol (FIGS. 2G-2H). The ratio of SatPC to total phospholipids was similar in surfactant from PAP patients and controls (FIG. 2I) consistent with the concept that the relative composition of surfactant phospholipid species is not altered in PAP[21]. In contrast, the ratio of cholesterol to total phospholipids in surfactant was significantly increased in PAP (FIG. 2K). Similarly, in $Csf2^{-/-}$ mice the ratio of SatPC to total phospholipids in surfactant was similar to WT mice and did not change with age (FIG. 2J). Importantly, the ratio of cholesterol to total phospholipids in surfactant was already elevated 3-fold in $Csf2^{-/-}$ mice at 6 weeks compared to WT, and remained elevated but did not increase further at 12, 24, and 36 weeks (FIG. 2L), whereas PAP lung disease severity increased steadily (FIG. 2B). Thus, in both humans and mice, disruption of GM-CSF signaling increases the amount of cholesterol relative to total phospholipids. Since reduction in alveolar macrophage numbers and/or functions can also cause surfactant accumulation to variable degrees comparable to GM-CSF deficiency[29,30], Applicant evaluated surfactant composition in other PAP-causing diseases and found that relative cholesterol content was increased (FIG. 2M) (Table 1). In summary, while the relative composition of surfactant phospholipids was not altered in PAP, the relative proportion of cholesterol in surfactant was increased.

TABLE 1

Mutations identified in congenital diseases of surfactant homeostasis

| Patient No. | Congenital Disease | Gene Mutation |
|---|---|---|
| 1 | ABCA3 Mutation | p.W1142X\p.W1142X |
| 2 | ABCA3 Mutation | p.W78X/p.S356Y |
| 3 | ABCA3 Mutation | R194G/F1203del |
| 4 | SFTPB Mutation | 121ins2/121ins2 |
| 5 | SFTPB Mutation | 121ins2/121ins2 |
| 6 | SFTPC Mutation | c.344C > T, p.Pro115Leu |
| 7 | SFTPC Mutation | c.271_279del9, TAT91_93del |
| 8 | SFTPC Mutation | c.89C > T, p.Pro30Leu |
| 9 | SFTPC Mutation | c.158_190dup, p.His64Proins11 |
| 10 | MARS Mutation | p.Ile285Thr/p.Arg497ter |

Cholesterol Drives Lipid Accumulation

To determine if surfactant lipid(s) may contribute to disruption of macrophage homeostasis, BMD macrophages from WT or $Csf2^{-/-}$ mice were exposed to PAP-surfactant or phospholipid-containing/cholesterol-free pharmaceutical surfactant (Survanta-surfactant) and then accumulation of cholesterol in macrophages was measured by a sensitive fluorometric method. PAP-surfactant exposure caused a marked increase in the levels of total, free, and, especially, esterified cholesterol in $Csf2^{-/-}$ macrophages and a smaller but highly significant increase in WT macrophages (FIGS. 3A-3C). In contrast, Survanta-surfactant exposure did not cause accumulation of either free or esterified cholesterol in either $Csf2^{-/-}$ or WT macrophages (FIGS. 3A-3C). To confirm this observation, BMD macrophages from WT and $Csf2^{-/-}$ mice were evaluated with or without exposure to either purified cholesterol-free Survanta-surfactant lipid extract (Survanta-lipids), or purified Survanta-lipids supplemented with free cholesterol. Exposure to Survanta-lipids did not cause cholesterol accumulation in either WT or $Csf2^{-/-}$ macrophages (FIG. 3D). In contrast, exposure to purified Survanta-lipids plus cholesterol caused marked accumulation of cholesterol in proportion to the fractional cholesterol exposure level in $Csf2^{-/-}$ macrophages and a smaller but significant degree of accumulation in WT macrophages (FIG. 3D). These results demonstrate that exposure to cholesterol but not to surfactant phospholipids caused cholesterol to accumulate in macrophages in the absence of GM-CSF signaling and to a lesser but significant level in WT macrophages, albeit, at a higher exposure level.

GM-CSF Regulates Cholesterol Clearance

To determine how GM-CSF regulates clearance of surfactant phospholipids and cholesterol in macrophages, Applicant first examined the kinetics of in vitro uptake and clearance of Survanta-surfactant spiked with rhodamine-labeled phosphatidylethanolamine by BMD macrophages from WT and $Csf2^{-/-}$ mice. Uptake of labeled Survanta-surfactant was similar in WT and $Csf2^{-/-}$ macrophages over a wide range of exposure levels as shown by the mean fluorescence intensity (MFI) of cells immediately after brief exposure (FIG. 3E). Clearance of labeled Survanta-surfactant was also similar in WT and $Csf2^{-/-}$ macrophages as shown by values for the half-life of phospholipid clearance: 1.43 and 1.74 hours, respectively (FIG. 3F). In contrast, pre-exposure to purified Survanta-surfactant lipids supplemented with cholesterol resulted in marked reduction (up to 80.5±2.1%) in subsequent uptake of labeled Survanta-surfactant by $Csf2^{-/-}$ macrophages in proportion to the fractional cholesterol content during prior exposure and a smaller but significant reduction by WT macrophages (FIG. 3G). Further, the half-life of cholesterol clearance was markedly increased in PAP-surfactant-exposed $Csf2^{-/-}$ macrophages compared to WT macrophages: half-life=21 hours versus 3.58 hours, respectively (FIG. 3H).

Figure 3I:
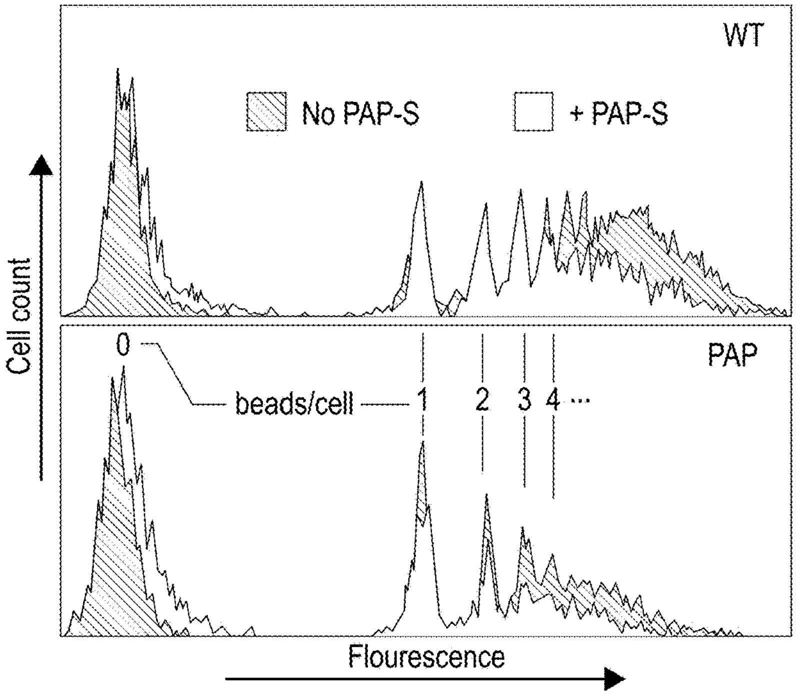
FIGS. 3I-3J, Phagocytosis of opsonized, fluorescent microspheres by BMD macrophages without and after exposure to PAP-S for 24 hours determined by flow cytometry and measurement of mean fluorescence intensity (MFI).
Figure 3J:
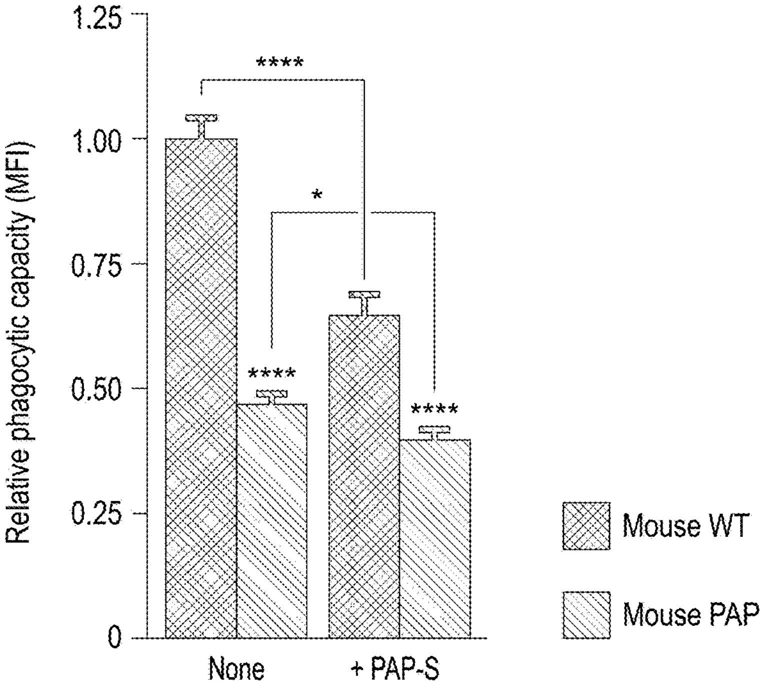

These results indicate that disruption of GM-CSF signaling does not impair the intrinsic capacity of macrophages to metabolize surfactant phospholipids, i.e. there is no major primary (intrinsic) defect in surfactant phospholipid catabolism in $Csf2^{-/-}$ macrophages. Rather, Applicant has discovered that disruption of GM-CSF signaling causes a primary macrophage defect in cholesterol clearance that results in a secondary reduction in both uptake and clearance of surfactant. Exposure to PAP-surfactant also impaired phagocytosis by BMD macrophages from both WT and Csf2rb−/− mice (FIGS. 3I-3J).

Figure 3K:
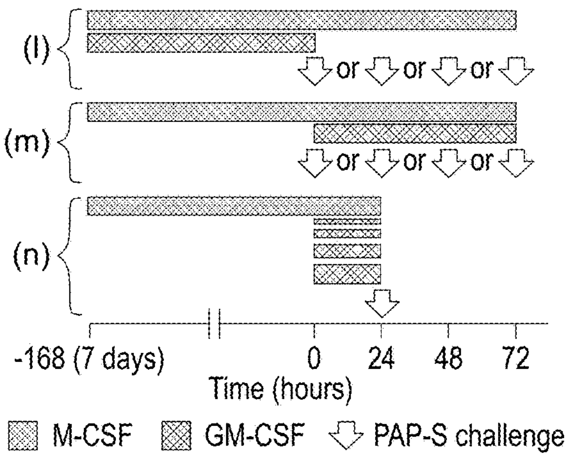
Figure 3L:
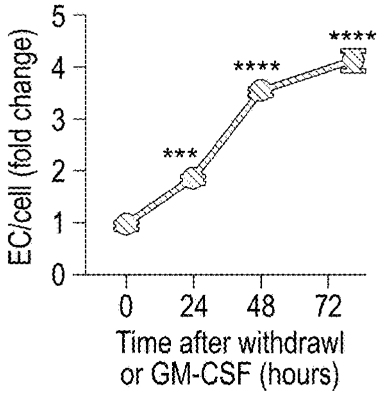
Figure 3M:
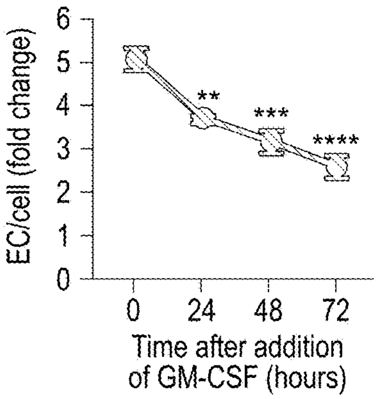
Figure 3N:
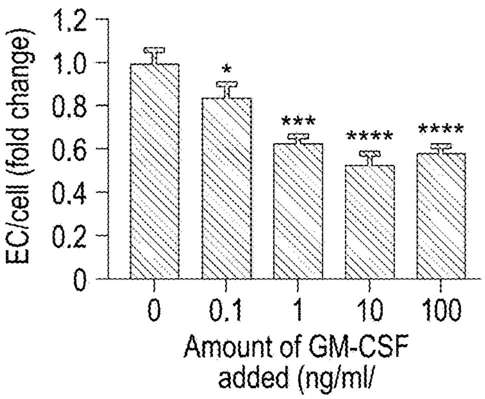

To further define the mechanism by which GM-CSF regulates cholesterol clearance, BMD macrophages were first cultured in M-CSF with (or without) GM-CSF and then GM-CSF was removed (or added-back) for various times (or at various concentrations) followed by exposure to PAP-surfactant and then measurement of intracellular cholesterol accumulation (FIG. 3K). Withdrawal of GM-CSF reduced the capacity of macrophages to clear cholesterol in a time-dependent way, which manifested as an 86% increase in exposure-related cholesterol ester accumulation by 24 hours that worsened to a 309% increase by 72 hours (FIG. 3L). Addition of GM-CSF to macrophages previously cultured without it increased the capacity of macrophages to clear cholesterol in a time-dependent way, which manifested as a 27% reduction in exposure-related cholesterol ester accumulation by 24 hours that improved to a 49% reduction by 72 hours (FIG. 3M). Further, GM-CSF increased the cholesterol clearance capacity of macrophages in dose-dependent fashion (FIG. 3N). These results indicate that regulation of cholesterol clearance in macrophages by GM-CSF is constitutive, reversible and concentration-dependent.

Cholesterol Homeostatic Pathway Regulation

The relative expression of PPARγ mRNA was markedly reduced in alveolar macrophages from Csf2$^{-/-}$ mice compared to WT mice (FIG. 4A) as was Abcg1 mRNA (FIG. 4B). In contrast, Abca1 mRNA was increased in Csf2$^{-/-}$ mice (FIG. 4C) in agreement with a previous report[23]. Alveolar macrophages from Csf2$^{-/-}$ mice also had reduced mRNA for several factors important in regulation of cholesterol homeostasis including Lxrα (liver X receptor alpha), Acat1 (cholesterol acetyltransferase 1), Nceh1 (neutral cholesterol ester hydrolase) and Lipa (lysosomal acid lipase) (FIGS. 7A-7D). Because ABCA1 and ABCG1 are involved in cholesterol clearance in macrophages and expression of both is abnormal in alveolar macrophages in humans and mice with PAP caused by disruption of GM-CSF mediated PPARγ signaling, Applicant determined if the changes in expression were primary (i.e., due to the loss of GM-CSF signaling) or secondary (i.e., due to exposure to surfactant). BMD macrophages from WT and Csf2$^{-/-}$ mice were exposed to PAP-surfactant or purified Survanta-surfactant lipids with or without added cholesterol. PPARγ mRNA levels were reduced in Csf2−/− macrophages compared to WT controls at baseline (FIG. 4D, left) and following exposure to PAP-surfactant were reduced further (FIG. 4D, right). Abcg1 mRNA was severely reduced in Csf2$^{-/-}$ macrophages compared to WT controls at baseline (FIG. 4E, left). After exposure to PAP-surfactant, Abcg1 mRNA was increased to higher than normal in WT macrophages and significantly increased in Csf2−/− macrophages, albeit still below normal (FIG. 4E, right). Abca1 mRNA levels were reduced in Csf2$^{-/-}$ macrophages compared to WT controls at baseline (FIG. 4F, left). After exposure to PAP-surfactant, Abca1 mRNA was markedly increased in Csf2$^{-/-}$ macrophages and unchanged in WT macrophages (FIG. 4F, right). To confirm these findings, BMD macrophages from Csf2$^{-/-}$ mice were exposed to purified Survanta-lipids with or without cholesterol supplementation. Exposure to purified, cholesterol-free Survanta-lipids did not alter Abcg1 or Abca1 mRNA levels in macrophages (FIGS. 4G-4H). In contrast, exposure to purified Survanta-surfactant lipids supplemented with cholesterol increased the level of Abcg1 mRNA (FIG. 4G) in proportion to the cholesterol content and also increased Abca1 mRNA to a smaller but significant degree (FIG. 4H). These results indicate that disruption of GM-CSF signaling caused a primary reduction in both Abca1 and Abcg1 mRNA in macrophages and that subsequent exposure to cholesterol-containing surfactant, but not cholesterol-free surfactant phospholipids, secondarily increased expression of both; resulting in higher-than-normal levels of Abca1 but only partial restoration of Abcg1 mRNA. GM-CSF signaling disruption also reduced alveolar macrophage mRNA for several factors critical to cholesterol homeostasis including Lxrα, Acat1, Nceh1, and Lipa (FIGS. 7A-7H).

Cholesterol Homeostasis as a Novel Therapeutic Target

Because PPARγ is a master transcriptional regulator of alveolar macrophage phenotype specification[36,37] and stimulates expression of both ABCA1 and ABCG1, molecules important in cholesterol export from macrophages[26,38], Applicant tested the hypothesis that pioglitazone, a thiazolidinedione capable of binding and activating PPARγ39, would increase the expression of Abca1 and Abcg1 in Csf2$^{-/-}$ macrophages and reduce the PAP disease severity after oral administration in Csf2rb$^{-/-}$ mice.

Figures 5A, 5B, 5C, 5D, 5E, 5F, 5G, 5H, 5I:
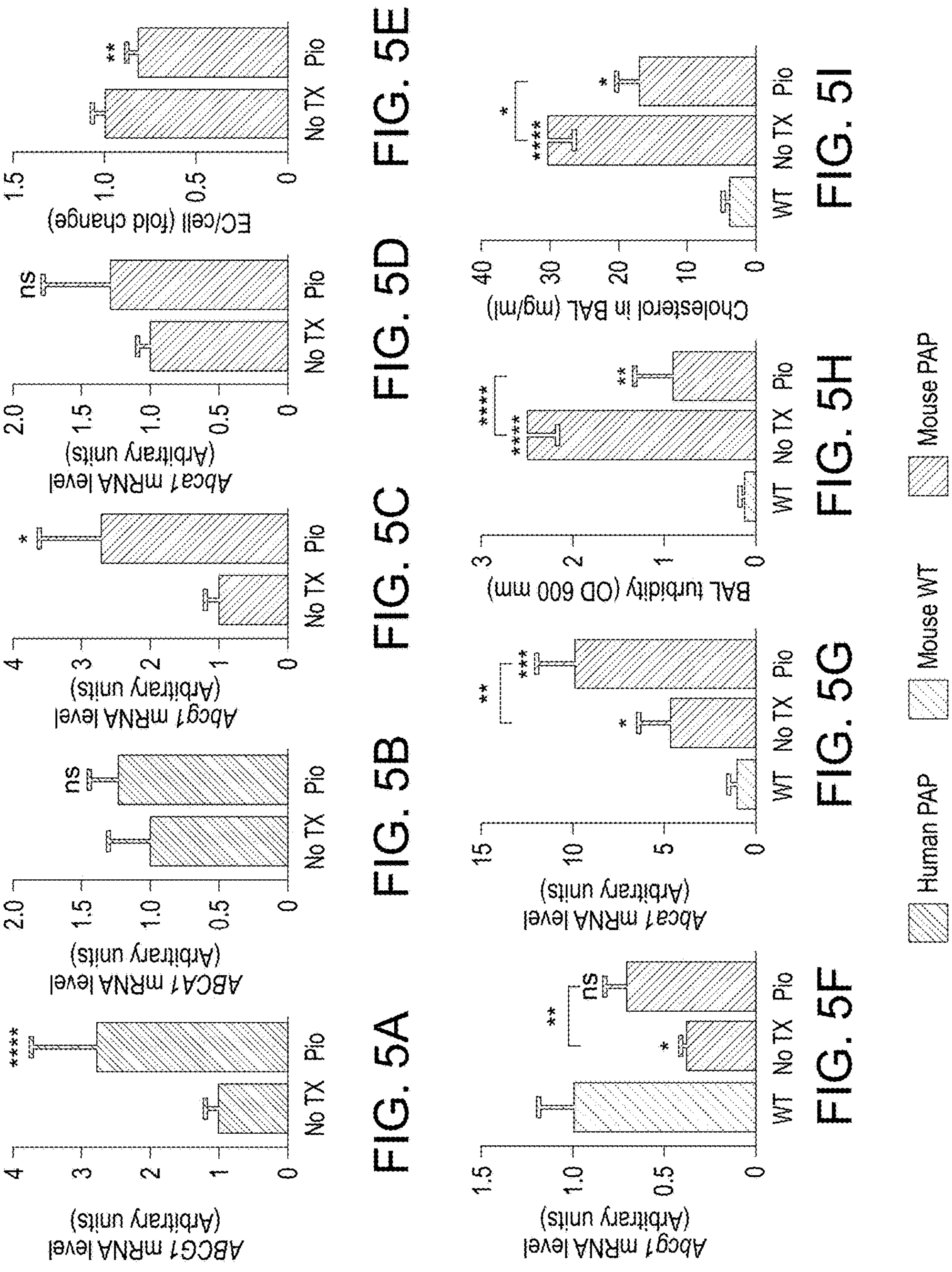
FIGS. 5A-5I. Pharmacologic targeting of cholesterol homeostasis in PAP.

Exposure of human alveolar macrophages from PAP patients to pioglitazone in vitro did not alter ABCA1 mRNA but markedly increased ABCG1 mRNA compared to untreated controls (FIGS. 5A-5B). Exposure of macrophages from PAP mice to pioglitazone had similar corresponding effects on Abcg1 and Abca1 mRNA levels (FIGS. 5C-5D) and reduced cholesterol ester accumulation following exposure to PAP-surfactant in vitro (FIG. 5E).

Since pioglitazone is available as an FDA-approved, commercially available, oral medication, we evaluated its efficacy as therapy of PAP in mice. Pioglitazone was administered to Csf2rb$^{-/-}$ mice orally by inclusion in the food to achieve a low-moderate dose (20 mg/kg/day) for six weeks. Pioglitazone treatment significantly increased levels of both Abca1 and Abcg1 mRNA in alveolar macrophages compared to untreated, age-matched controls (FIGS. 5F-5G). It also significantly reduced BAL turbidity (FIG. 5H) and cholesterol level in Csf2rb$^{-/-}$ mice compared to untreated, age-matched controls (FIG. 5I). Oral pioglitazone had no apparent adverse effects in Csf2rb$^{-/-}$ mice (not shown). These results identify PPARγ as a molecular target for regulating cholesterol homeostasis in the lungs and support the feasibility of pioglitazone as a novel pharmacologic therapy of PAP.

Because LXRα also regulates ABCA1 and ABCG1 expression[40], Applicant evaluated it as a second molecular target. In vitro exposure of alveolar macrophages from PAP patients to T0901317, and previously evaluated as a potential cholesterol-related therapy of atherosclerosis[41], caused an increase in ABCG1 and ABCA1 mRNA (FIGS. 8A-8B) consistent with known effects of this transcriptional regulator[42,43]. Similarly, in vitro exposure of BMD macrophages from Csf2$^{-/-}$ mice to T0901317 increased Abcg1 and Abca1 mRNA levels (FIGS. 8C-8D) and reduced cholesterol ester accumulation following exposure to PAP-surfactant (FIG. 8E). Oral administration of T0901317 to Csf2rb$^{-/-}$ mice (10 mg/kg/day, 7 days) significantly increased Abcg1 and Abca1 mRNA levels in alveolar macrophages compared to untreated, age-matched controls (FIGS. 8F-8G). These preclinical results support the potential feasibility of LXR as a cholesterol-related molecular target for pharmacotherapy of PAP.

Applicant has identified mechanisms by which GM-CSF regulates lipid homeostasis in macrophages, which is critical to surfactant homeostasis, alveolar stability and lung function, and by which disruption of GM-CSF signaling causes PAP syndrome. GM-CSF stimulated cholesterol clearance in macrophages in a constitutive, reversible, and concentration-dependent manner. Loss of GM-CSF stimulation caused macrophage foam-cell formation after surfactant exposure and altered lung surfactant composition by increasing the relative proportion of cholesterol. PPARγ and LXRα were identified by applicant as molecular targets for cholesterol-related pharmacotherapy of PAP.

Figure 6:
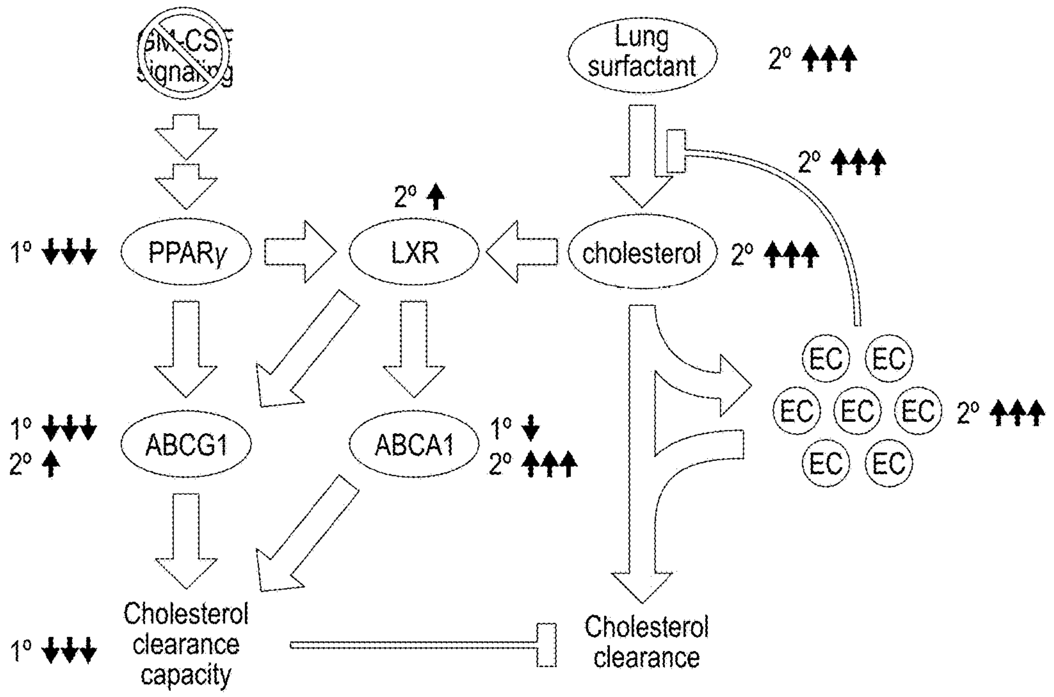
FIG. 6. Proposed mechanism by which GM-CSF regulates cholesterol homeostasis in alveolar macrophages and its disruption causes PAP. Shown are signaling pathways (blue arrows), the primary effects of GM-CSF signaling disruption (green numbers/arrows) and the secondary consequences of exposure to cholesterol-containing surfactant (red numbers/arrows).

Disruption of GM-CSF signaling caused a complex pattern of macrophage defects including primary abnormalities attributable directly to the loss of GM-CSF stimulation and secondary abnormalities resulting from subsequent exposure to surfactant (FIG. 6). Primary defects, which were not limited to lung macrophages, included suppression of the GM-CSF>PU·1>PPARγ signaling axis, reduced expression of ABCG1 and other cholesterol clearance-related genes and reduced cholesterol clearance capacity but did not result in an inability to catabolize surfactant phospholipids. Secondary abnormalities, which occurred only after exposure to cholesterol-containing surfactant, included foam-cell formation and reduction in surfactant uptake and clearance, and increased expression of cholesterol-stimulated, LXR-target genes such as ABCA1[42]. Phagocytic function was reduced primarily by the absence of GM-CSF and secondarily by exposure to cholesterol-containing surfactant in both normal and PAP macrophages. The mechanism identified explains Golde's 'stuffed macrophage' hypothesis of PAP pathogenesis[44] and explains why cytopathologic abnormalities occur in alveolar but not other tissue macrophages and also their pattern of ABCA1 and ABCG1 expression[23]. The accumulation of cholesterol in alveolar macrophages has implications for the increased infection risk in PAP[45] since facultative intracellular organisms such as mycobacteria, particularly *M tuberculosis*, preferentially invade and replicate in alveolar macrophages, can themselves induce foam-cell formation[46] and utilize cholesterol as a carbon source[47,48], which may promote persistence[47].

The observation of an increased ratio of cholesterol to phospholipid in human and murine PAP challenges the concept that PAP arises from accumulation of surfactant of essentially normal lipid composition[15,21]. Importantly, the latter view derives largely from studies restricted to evaluating the polar lipid fraction of surfactant[20] rather than total surfactant lipids as in Applicant's study.

Applicant's findings are supported by a report focused to surfactant proteins in PAP that incidentally noted an increase in cholesterol and another reporting an increase in cholesterol in alveolar macrophages in PAP[23,49,50]. Applicant's results also agree with a previous report indicating surfactant phospholipids and cholesterol are metabolized in macrophages via distinct pathways[51] and extend it by showing that a reduction in cholesterol clearance results in formation of foam-cells with secondarily impaired uptake and clearance of surfactant phospholipids.

These results have clinical implications for pharmacotherapy of autoimmune PAP, hereditary PAP, other surfactant-related lung diseases, and possibly other diseases associated with macrophage foam-cell formation. The observation that GM-CSF constitutively regulates cholesterol clearance relates to the timing of administration of inhaled GM-CSF as pharmacotherapy of PAP, which is currently prescribed 'off-label' once daily on alternating weeks[52]. The observation that pioglitazone increased ABCG1 expression in macrophages, reduced cholesterol accumulation, and reduced disease severity in PAP mice supports its use as pharmacotherapy of PAP in humans. It is interesting that pioglitazone was recently shown to reduce the risk of stroke or myocardial infarction in patients with insulin resistance[53]. These results have mechanistic implications for this clinical observation related to potential for improving cholesterol export by foam-cells within atherosclerotic plaques. That T0901317 had similar effects on ABCG1 expression and cholesterol clearance suggests that targeting LXR activity may be another feasible pharmacotherapeutic approach.

Methods

Bronchoalveolar lavage and alveolar macrophage collection in human participants. This study was conducted with the approval of the Cincinnati Children's Hospital Medical Center institutional review board and all participants or their legal guardians gave written informed consent. Human BAL fluid and alveolar macrophages were obtained from BAL using flexible bronchoscopy or from discarded material of PAP patients undergoing therapeutic whole lung lavage. After the fluid was centrifuged at 283 g for 10 minutes, the cellular pellet was re-suspended in the culture medium. Human alveolar macrophages were isolated by adherence to tissue culture plastic. Extracellular debris was removed by gentle washing with PBS.

Bronchoalveolar lavage and alveolar macrophage collection in mice. GM-CSF (CSF2) knockout ($Csf2^{-/-}$) mice5 and Csf2rb gene-deficient ($Csf2rb^{-/-}$)14 were reported previously (referred to mouse PAP). C57B1/6 mice (referred to as wild type or WT mice) were purchased from Charles River. All mice were bred, housed, and studied in the Cincinnati Children's Research Foundation Vivarium using protocols approved by the Institutional Animal Care and Use Committee. Epithelial lining fluid and non-adherent cells were collected from indicated mice by bronchoalveolar lavage (BAL) using five lml aliquots of PBS plus 0.5 mM EDTA4. The 1 ml aliquots were pooled and the recovered volumes recorded. The supernatant was removed and the cellular pellets were re-suspended in the culture media for isolation of alveolar macrophages by adherence to tissue culture plastic.

Macrophage Morphology

Diff-Quick staining. Cells were sedimented and stained with buffered eosin and methylene blue (Diff-Quick, Fischer) and evaluated by light microscopy Oil red O staining. Cells were stained with Oil Red O staining using the Oil red O staining kit (Poly Scientific R&D Corporation) according to the following protocol. Briefly, cells were fixed with 4% PFA and washed twice with distilled water. Cells were placed in absolute propylene glycol for 5 minutes. Propylene glycol was removed and cells stained in a 0.5% oil red o solution in propylene glycol for 30 minutes. Cells were rinsed in an 85% propylene glycol solution for 5 minutes and washed twice with distilled water followed by a hematoxylin counterstain for 2 minutes. Cells were mounted with an aqueous mounting medium such as glycerin jelly and evaluated by light microscopy.

Electron microscopy. Alveolar macrophages were collected by centrifugation (3,000 rpm, 3 min, RT), incubated in modified Karnovky's fixative (2% paraformaldehyde and 2% glutaraldehyde in 0.1 M sodium cacodylate buffer plus 0.1% calcium chloride, pH 7.3, 2 hr, RT), and cell blocks were prepared as previously described 7.

Tri-one dimensional thin layer chromatography (TOD-TLC) analysis. Alveolar macrophages were isolated from BALF based on adherence to tissue culture plastic as described above. Cellular lipids analysis was performed on AMs isolated from individual WT mice and two pooled mice per sample for $Csf2^{-/-}$ mice. Cells were repeatedly washed with PBS to remove extracellular surfactant and then 100% isopropanol was added to the tissue culture wells, 2 mls for a 6-well plate. Cellular lipids were extracted for 2 hrs at room temperature or overnight at 40C. The isopropanol was then transferred into glass tubes and half the volume of new isopropanol was added back into the tissue culture plate for 30 minutes to recover any remaining sample and combined with the original volume. Lipid samples were then evaporated using a stream of nitrogen and a water bath set to 52° C. Cellular lipid samples were then loaded onto high performance thin layer chromatography plates pre-coated with silica gel 60 (Fisher). Plates were prewashed with chloroform and methanol to remove any contaminants and dried overnight at 1200C. Plates were developed in a solvent system modified from White et al54. Briefly, plates were first developed in a Solvent mixture of chloroform, ethanol, triethylamine, and water (30:35:35:6) up to 7 centimeters of a ten centimeter plate. Plates are removed from the chamber, dried, and placed in a second solvent of hexane and diethylether (90:10) up to nine centimeters of a ten centimeter plate. Plates are again removed from the chamber, dried, and then placed in the final solvent of pure hexane and run to the top of the plate. Bands are visualized by spraying with a 0.05% solution of premuline in acetone and water (80:20) and detected as ultraviolet spots at 366 nm on a Typhoon 9500 molecular imager54.

Tissue macrophage differentiation and culture. All cells were maintained in the culture medium of Dulbecco's modified eagle's medium (DMEM) (Life Technologies) plus 10% FBS, 50 U ml-1 penicillin, and 50 μg ml-1 streptomycin. Bone marrow cells were obtained from 6-8-week-old mice by flushing the tibias and femurs with the culture media described above.

Mononuclear cells were isolated by centrifugation over a Ficoll-Paque (GE Healthcare Life Sciences) gradient at room temperature for 30 minutes. The buffy coat was washed in PBS and the cellular pellet re-suspended in the culture medium with M-CSF (R&D Systems) (5 ng/ml) plus or minus GM-CSF (R&D Systems) as dictated per experimental requirements. Cells were cultured in a 10 cm dish overnight at 37° C. and the next day non-adherent cells were recovered and transferred to a new dish and cultured under the same conditions for an additional 24 hrs. At this stage non-adherent cells were discarded and adherent cells cultured for an additional five days to allow differentiation of bone marrow derived (BMD) macrophages. Peritoneal macrophages were isolated from the peritoneal without chemical solicitation by washing with 8 ml of PBS plus 0.5 mM EDTA. WT peritoneal macrophages were cultured in vitro in culture medium with M-CSF (5 ng/ml) and GM-CSF (long/ml), and $Csf2^{-/-}$ peritoneal macrophages were cultured in culture medium with M-CSF alone.

Bronchoalveolar lavage fluid analysis.

Cholesterol levels. Total and free cholesterol levels were measured by the amplex red cholesterol assay (Life Technologies) per the manufacturer's protocol. Esterified cholesterol was then calculated by subtracting free cholesterol from the total value.

Turbidity. The turbidity of the fluid was measured as previously described[4,55] Briefly, 250 uls of the BAL were diluted into 750 uls of PBS and the optical density measured at a wavelength of 600 nm and multiplied by the dilution factor.

Phospholipid levels. Aliquots of the BAL were taken as pre-spun samples and total BAL lipids were extracted using chloroform and methanol. Total phosphate and saturated phosphatidylcholine were measured as previously reported[56,57].

In vitro surfactant challenge assay. BMD macrophages or peritoneal macrophages were seeded at $4\times10^5$ cells per well of a 12 well tissue culture plate and allowed to adhere with fresh media and cytokines overnight. Cells were then challenged for 24 hrs with pulmonary surfactant isolated from a hereditary PAP patient (PAP-S). After the challenge cells were gently washed with PBS to remove exogenous PAP-S and cellular lipids were then extracted and analyzed by the amplex red cholesterol assay.

Liposome and fluorescently labeled surfactant preparation. Lipids, cholesterol or rhodamine-dipalmitoyl phosphatidylethanolamine (R-DPPE), were purchased from Avanti Polar Lipids as organic solutions in chloroform. Survanta lipids (Sv-S) (Abbvie) were extracted using chloroform and methanol and to the extracted chloroform phase the additional lipids, cholesterol or R-DPPE, were combined in a glass tube and vortexed. Solvents were evaporated using a stream of nitrogen and a water bath at 52° C. PBS prewarmed to 37° C. was added to the dried lipids and placed in a 45° C. water bath for 15 minutes. Samples were removed and immediately vortexed, this process was repeat twice. Using a bath sonicator the samples were briefly sonicated and transferred to a glass vial with a Teflon lined cap before use. For experiments involving fluorescently labeled surfactant Sv-S was chloroform methanol extracted and fluorescently labeled lipids were added to the extracted Survanta samples in chloroform and vortexed vigorously. Samples were dried and the above listed procedure used to prepare liposomes. Cells were challenged at a final concentration of 250 ug/ml of total lipid with the fluorescent label present at a 1:10 ratio. Uptake experiments were performed for 30 minutes at 37° C. as previously reported[58]. Cells were collected, fixed, and analyzed by flow cytometry. Kinetic experiments were performed by loading cells for 24 hrs with fluorescently labeled surfactant. Extracellular surfactant was removed by gentle washing with PBS. Cells were collected for an immediate loaded time point or 3 hr, 8 hr, and 24 hrs after washing.

Cholesterol reconstitution studies. Free cholesterol was added to chloroform and methanol extracted Sv-S lipids in chloroform and liposomes were prepared as previously described. Sv-S or Sv-S plus cholesterol at 250 ug/ml was then used as a lipid source to challenge macrophages in vitro for 24 hrs. After the challenge cells were gently washed with PBS and cellular lipids were extracted or RNA isolated and analyzed as previously described. For examining cholesterol dependent effects on surfactant uptake macrophages were pre-challenged for 24 hrs with Sv-S or Sv-S plus cholesterol. Following the pre-challenge period cells were washed gently with PBS to remove exogenous lipid and challenged for an additional 30 minutes with R-DPPE labeled Sv-S at 37° C. Cells were washed with PBS and immediately fixed with 4% PFA. Surfactant uptake was measured by flow cytometry detection of R-DPPE inside the cells.

Kinetics of cholesterol clearance. For kinetic experiments $Csf2^{-/-}$ BMD macrophages were differentiated and maintained throughout the course of the study in M-CSF while WT BMD macrophages received both M-CSF and GM-CSF. On the 7th day cells were seeded into 12 well plates and allowed to adhere overnight in fresh media with cytokines. Cells were then challenged with PAP-S for 24 hrs. Cells were collected immediately, as a loaded control, and 3, 8, 24, 48, and 72 hrs after washing to remove PAP-S to track changes in cholesterol homeostasis overtime. Cellular lipids were extracted, normalized to total protein, and analyzed.

Phagocytosis assay. The phagocytic capacity of WT and Csf2rb−/− BMD macrophages after PAP-S challenge was evaluated using opsonized Nile red beads (Spherotech) as described previously[59] (. The mean fluorescence intensity of the phagocytosed beads was measured using FACS Canto 1 (BD biosciences) and histogram overlays was done using FlowJo software.

GM-CSF Plasticity Sudies.

GM-CSF withdrawal. $Csf2^{-/-}$ BMD macrophages were differentiated and maintained in media containing M-CSF and GM-CSF. After 7 days of differentiation cells were split into 12well tissue culture plates and allowed to adhere overnight in GM-CSF containing media. The following day the media was changed to M-CSF only and cells were challenged with PAP-S for 24hrs immediately or 24, 48, and 72 hours after GM-CSF withdrawal. Cellular lipids were extracted, normalized to total protein, and analyzed. $Csf2^{-/-}$ BMD macrophages were used to ensure elimination of any potential autologous GM-CSF expression-related stimulation.

Multi-Day GM-CSF stimulation. $Csf2^{-/-}$ BMD macrophages were generated in media containing M-CSF. On the 7th day cells were stimulated for 0, 24, 48, or 72 hrs with 10 ng/ml of GM-CSF before 24 hr surfactant challenge with PAP-S. Cellular lipids were extracted, normalized to total protein, and analyzed.

GM-CSF dose response. $Csf2^{-/-}$ BMD macrophages were generated in media containing M-CSF. On the 7th day cells were stimulated by a dose response of GM-CSF (0, 0.1,1,10, and 100 ng/ml) for 24 hrs before surfactant challenge with PAP-S. Cellular lipids were extracted, normalized to total protein, and analyzed.

RNA isolation and gene expression analysis. Total RNA was isolated using Trizol (Life Technologies) and was converted to cDNA using the Invitrogen Superscript III first strand synthesis kit (Life Technologies) according to the manufacturer's protocol. Standard quantitative RT-PCR (qRT-PCR) was performed as previously described 10 on an Applied Biosystems 7300 Real-Time PCR System (Life Technologies) to measure transcript abundance using TaqMan® oligonucleotide primer sets (all from Life Technologies). Expression of target genes was normalized to the expression of 18s RNA.

Molecular Therapy Experiments

Ex vivo human PPARγ & LXR stimulation studies. After purifying alveolar macrophages, fresh media was added to the adherent alveolar macrophages containing human M-CSF (R&D) (25ng/ml) only or M-CSF plus Pioglitazone (Sigma) (10 μM) or T0901317 (Tocris) (1 μM) for 24 hrs. qRT-PCR was performed as described above.

In vitro mouse PPARγ & LXR stimulation Studies. BMD macrophages were prepared as previously described in the presence of M-CSF (10 ng/ml). On the 7th day macrophages were stimulated for 24 hrs with M-CSF (10 ng/ml), GM-CSF (10 ng/ml), Pioglitazone (10 μm) or T0901317 (1 μm from Tocris). Macrophages were then used for an in vitro surfactant challenge assay or gene expression analysis by qRT-PCR as described above.

In vivo PPARγ stimulation studies. Pioglitazone was incorporated into standard rodent chow at a dose expected to deliver 20 mg/kg BW/Day. BAL turbidity and alveolar macrophage gene expressions were measured as described above. GM-CSF levels and total cholesterol levels in the BAL were measured in the supernatant of fluid after centrifuge at 283 g for 10 minutes at 4° C. by enzyme-linked immunosorbent assay (ELISA) (R&D systems) and Amplex Red Cholesterol assay respectively as described above.

In vivo LXR Stimulation Studies. Mice were administered T0901317 by oral gavage once daily for 7 days at a dose of 10 mg/kg/BW/Day using propylene glycol and tween 80 as a vehicle. On the 7th day alveolar macrophages were collected by bronchoalveolar lavage. Following brief adherence to tissue culture plastic to remove BAL debris, alveolar macrophages were then used for RNA isolation and gene expression analysis by qRT-PCR as described above

REFERENCES

1 Hamilton, J. A. Colony-stimulating factors in inflammation and autoimmunity. Nat Rev Immunol 8, 533-544 (2008).

2 Guilliams, M. et al. Alveolar macrophages develop from fetal monocytes that differentiate into long-lived cells in the first week of life via GM-CSF. J Exp Med 210, 1977-1992, doi:10.1084/jem.20131199 (2013).

3 Trapnell, B. C., Whitsett, J. A. & Nakata, K. Pulmonary alveolar proteinosis. N Engl J Med 349, 2527-2539, doi: 10.1056/NEJMra023226349/26/2527 [pii] (2003).

4 Suzuki, T. et al. Pulmonary macrophage transplantation therapy. Nature 514, 450-454, doi:10.1038/nature13807 (2014).

5 Dranoff, G. et al. Involvement of granulocyte-macrophage colony-stimulating factor in pulmonary homeostasis. Science 264, 713-716 (1994).

6 Stanley, E. et al. Granulocyte/macrophage colony-stimulating factor-deficient mice show no major perturbation of hematopoiesis but develop a characteristic pulmonary pathology. Proc Natl Acad Sci U S A 91, 5592-5596 (1994).

7 Sakagami, T. et al. Patient-derived granulocyte/macrophage colony-stimulating factor autoantibodies reproduce pulmonary alveolar proteinosis in nonhuman primates. Am J Respir Crit Care Med 182, 49-61, doi:10.1164/rccm.201001-00080C (2010).

8 Kitamura, T. et al. Idiopathic pulmonary alveolar proteinosis as an autoimmune disease with neutralizing antibody against granulocyte/macrophage colony-stimulating factor. J Exp Med 190, 875-880 (1999).

9 Sakagami, T. et al. Human GM-CSF autoantibodies and reproduction of pulmonary alveolar proteinosis. N Engl J Med 361, 2679-2681, doi:361/27/2679 [pii]10.1056/NEJMc0904077 (2009).

10 Suzuki, T. et al. Familial pulmonary alveolar proteinosis caused by mutations in CSF2RA. J Exp Med 205, 2703-2710, doi:j em.20080990 [pii]10.1084/jem.20080990 (2008).

11 Martinez-Moczygemba, M. et al. Pulmonary alveolar proteinosis caused by deletion of the GM-CSFRalpha gene in the X chromosome pseudoautosomal region 1. J Exp Med 205, 2711-2716 (2008).

12 Suzuki, T. et al. Hereditary pulmonary alveolar proteinosis caused by recessive CSF2RB mutations. Eur Respir J 37, 201-204, doi:10.1183/09031936.00090610 (2011).

13 Tanaka, T. et al. Adult-onset hereditary pulmonary alveolar proteinosis caused by a single-base deletion in CSF2RB. J Med Genet 48, 205-209, doi:10.1136/jmg.2010.082586 (2011).

14 Robb, L. et al. Hematopoietic and lung abnormalities in mice with a null mutation of the common beta subunit of the receptors for granulocyte-macrophage colony-stimulating factor and interleukins 3 and 5. Proc Natl Acad Sci U S A 92, 9565-9569 (1995).

15 Yoshida, M., Ikegami, M., Reed, J. A., Chroneos, Z. C. & Whitsett, J. A. GM-CSF regulates protein and lipid catabolism by alveolar macrophages. Am J Physiol Lung Cell Mol Physiol 280, L379-386 (2001).

16 Perez-Gil, J. & Weaver, T. E. Pulmonary surfactant pathophysiology: current models and open questions. Physiology (Bethesda) 25, 132-141, doi:10.1152/physio1.00006.2010 (2010).

17 Veldhuizen, R., Nag, K., Orgeig, S. & Possmayer, F. The role of lipids in pulmonary surfactant. Biochim Biophys Acta 1408, 90-108 (1998).

18 Daniels, C. B., Barr, H. A., Power, J. H. & Nicholas, T. E. Body temperature alters the lipid composition of pulmonary surfactant in the lizard Ctenophorus nuchalis. *Exp Lung Res* 16, 435-449 (1990).

19 Gurel, O., Ikegami, M., Chroneos, Z. C. & Jobe, A. H. Macrophage and type II cell catabolism of SP-A and saturated phosphatidylcholine in mouse lungs. *Am J Physiol Lung Cell Mol Physiol* 280, L1266-1272 (2001).

20 Griese, M. Pulmonary surfactant in health and human lung diseases: state of the art. *Eur Respir J* 13, 1455-1476 (1999).

21 Ikegami, M. et al. Surfactant metabolism in transgenic mice after granulocyte macrophage-colony stimulating factor ablation. *Am J Physiol* 270, L650-658 (1996).

22 Pison, U., Wright, J. R. & Hawgood, S. Specific binding of surfactant apoprotein SP-A to rat alveolar macrophages. *Am J Physiol* 262, L412-417. (1992).

23 Thomassen, M. J. et al. ABCG1 is deficient in alveolar macrophages of GM-CSF knockout mice and patients with pulmonary alveolar proteinosis. *J Lipid Res* 48, 27622768, doi:10.1194/jlr·P700022-JLR200 (2007).

24 Bonfield, T. L. et al. Peroxisome proliferator-activated receptor-gamma is deficient in alveolar macrophages from patients with alveolar proteinosis. *Am J Respir Cell Mol Biol* 29, 677-682 (2003).

25 Ditiatkovski, M., Toh, B. H. & Bobik, A. GM-CSF deficiency reduces macrophage PPAR-gamma expression and aggravates atherosclerosis in ApoE-deficient mice. *Arterioscler Thromb Vasc Biol* 26, 2337-2344, doi: 01.ATV.0000238357.60338.90 [pii]10.1161/01.ATV.0000238357.60338.90 (2006).

26 Cavelier, C., Lorenzi, I., Rohrer, L. & von Eckardstein, A. Lipid efflux by the ATP-binding cassette transporters ABCA1 and ABCG1. *Biochim Biophys Acta* 1761, 655-666, doi:10.1016/j.bbalip.2006.04.012 (2006).

27 Ramirez-Zacarias, J. L., Castro-Munozledo, F. & Kuri-Harcuch, W. Quantitation of adipose conversion and triglycerides by staining intracytoplasmic lipids with Oil red O. Histochemistry 97, 493-497 (1992).

28 Mehlem, A., Hagberg, C. E., Muhl, L., Eriksson, U. & Falkevall, A. Imaging of neutral lipids by oil red O for analyzing the metabolic status in health and disease. Nat Protoc 8, 1149-1154, doi:10.1038/nprot.2013.055 (2013).

29 Trapnell, B. C. & Luisetti, M. in Murray & Nadel's Textbook of Respiratory Medicine (ed Mason R.C. Broaddus V.C., Ernst J.D., King T.E., Lazarus S.C., Murray J.F., Nadel J.A., Slutsky A., Gotway M.) Ch. 70, (Elsevier Health Sciences, 2015).

30 Forbes, A. et al. Alveolar macrophage depletion is associated with increased surfactant pool sizes in adult rats. J Appl Physiol 103, 637-645 (2007).

31 Okazaki, H. et al. Identification of neutral cholesterol ester hydrolase, a key enzyme removing cholesterol from macrophages. J Biol Chem 283, 33357-33364, doi:10.1074/jbc.M802686200 (2008).

32 Igarashi, M. et al. The critical role of neutral cholesterol ester hydrolase 1 in cholesterol removal from human macrophages. Circ Res 107, 1387-1395, doi:10.1161/CIRCRESAHA.110.226613 (2010).

33 Ouimet, M. et al. Autophagy regulates cholesterol efflux from macrophage foam cells via lysosomal acid lipase. Cell Metab 13, 655-667, doi:10.1016/j.cmet.2011.03.023 (2011).

34 Ishii, I. et al. Beta-VLDL-induced cholesterol ester deposition in macrophages may be regulated by neutral cholesterol esterase activity. Arteriosclerosis and thrombosis : a journal of vascular biology/American Heart Association 12, 1139-1145 (1992).

35 Kritharides, L., Christian, A., Stoudt, G., Morel, D. & Rothblat, G. H. Cholesterol metabolism and efflux in human THP-1 macrophages. Arterioscler Thromb Vasc Biol 18, 1589-1599 (1998).

36 Schneider, C. et al. Induction of the nuclear receptor PPAR-gamma by the cytokine GM-CSF is critical for the differentiation of fetal monocytes into alveolar macrophages. *Nature immunology* 15, 1026-1037, doi:10.1038/ni.3005 (2014).

37 Baker, A. D. et al. PPARgamma regulates the expression of cholesterol metabolism genes in alveolar macrophages. *Biochem Biophys Res Commun* 393, 682-687, doi: 50006-291X(10)00276-7 [pii]10.1016/j.bbrc.2010.02.056 (2010).

38 Out, R. et al. Macrophage ABCG1 deletion disrupts lipid homeostasis in alveolar macrophages and moderately influences atherosclerotic lesion development in LDL receptor-deficient mice. *Arterioscler Thromb Vasc Biol* 26, 2295-2300, doi:10.1161/01.ATV.0000237629.29842.4c (2006).

39 Lehmann, J. M. et al. An antidiabetic thiazolidinedione is a high affinity ligand for peroxisome proliferator-activated receptor gamma (PPAR gamma). *J Biol Chem* 270, 12953-12956 (1995).

40 Ozasa, H. et al. Pioglitazone enhances cholesterol efflux from macrophages by increasing ABCA1/ABCG1 expressions via PPARgamma/LXRalpha pathway: findings from in vitro and ex vivo studies. *Atherosclerosis* 219, 141-150, doi:10.1016/j.atherosclerosis.2011.07.113 (2011).

41 Levin, N. et al. Macrophage liver X receptor is required for antiatherogenic activity of LXR agonists. *Arterioscler Thromb Vasc Biol* 25, 135-142, doi:10.1161/01.ATV.0000150044.84012.68 (2005).

42 Venkateswaran, A. et al. Control of cellular cholesterol efflux by the nuclear oxysterol receptor LXR alpha. *Proc Natl Acad Sci USA* 97, 12097-12102, doi:10.1073/pnas.200367697 (2000).

43 Laffitte, B. A. et al. LXRs control lipid-inducible expression of the apolipoprotein E gene in macrophages and adipocytes. *Proc Natl Acad Sci USA* 98, 507-512, doi:10.1073/pnas.021488798 (2001).

44 Golde, D. W. Alveolar proteinosis and the overfed macrophage [editorial]. *Chest* 76, 119120 (1979).

45 Uchida, K. et al. GM-CSF autoantibodies and neutrophil dysfunction in pulmonary alveolar proteinosis. *N Engl J Med* 356, 567-579, doi:356/6/567 [pii]10.1056/NEJMoa062505 (2007).

46 Daniel, J., Maamar, H., Deb, C., Sirakova, T. D. & Kolattukudy, P. E. Mycobacterium tuberculosis uses host triacylglycerol to accumulate lipid droplets and acquires a dormancy-like phenotype in lipid-loaded macrophages. *PLoS Pathog* 7, e1002093, doi:10.1371/journal.ppat.1002093 (2011).

47 Pandey, A. K. & Sassetti, C. M. Mycobacterial persistence requires the utilization of host cholesterol. *Proc Natl Acad Sci USA* 105, 4376-4380, doi:10.1073/pnas.0711159105 (2008).

48 Griffin, J. E. et al. Cholesterol catabolism by Mycobacterium tuberculosis requires transcriptional and metabolic adaptations. *Chem Biol* 19, 218-227, doi:10.1016/j.chembio1.2011.12.016 (2012).

49 Doyle, I. R. et al. Quantity and structure of surfactant proteins vary among patients with alveolar proteinosis. *Am J Respir Crit Care Med* 157, 658-664 (1998).

50 Abe, A. et al. Lysosomal phospholipase A2 is selectively expressed in alveolar macrophages. *J Biol Chem* 279, 42605-42611, doi:10.1074/jbc.M407834200M407834200 [pii] (2004).

51 Hawgood, S. & Poulain, F. R. The pulmonary collectins and surfactant metabolism. *Annu Rev Physiol* 63, 495-519 (2001).

52 Tazawa, R. et al. Inhaled granulocyte/macrophage-colony stimulating factor as therapy for pulmonary alveolar proteinosis. *Am J Respir Crit Care Med* 181, 1345-1354, doi:200906-0978OC [pii]10.1164/rccm.200906-0978OC (2010).

53 Kernan, W. N. et al. Pioglitazone after Ischemic Stroke or Transient Ischemic Attack. *New England Journal of Medicine* 374, 1321-1331, doi:doi:10.1056/NEJMoa1506930 (2016).

54 White, T., Bursten, S., Federighi, D., Lewis, R. A. & Nudelman, E. High-resolution separation and quantification of neutral lipid and phospholipid species in mammalian cells and sera by multi-one-dimensional thin-layer chromatography. *Anal Biochem* 258, 109-117, doi:10.1006/abio.1997.2545 (1998).

55 Suzuki, T. et al. Hereditary pulmonary alveolar proteinosis: pathogenesis, presentation, diagnosis, and therapy. *Am J Respir Crit Care Med* 182, 1292-1304, doi:10.1164/rccm.201002-0271OC (2010).

56 Bridges, J. P. et al. Orphan G protein-coupled receptor GPR116 regulates pulmonary surfactant pool size. *Am J Respir Cell Mol Biol* 49, 348-357, doi:10.1165/rcmb.2012-0439OC (2013).

57 Baker, A. D. et al. Targeted PPAR{gamma} deficiency in alveolar macrophages disrupts surfactant catabolism. *J Lipid Res* 51, 1325-1331, doi:jlr.M001651 [pii] 10.1194/jlr.M001651 (2010).

58 White, T., Bursten, S., Federighi, D., Lewis, R. A. & Nudelman, E. High-resolution separation and quantification of neutral lipid and phospholipid species in mammalian cells and sera by multi-one-dimensional thin-layer chromatography. *Anal Biochem* 258, 109-117, doi:10.1006/abio.1997.2545 (1998).

59 Yoshida, M., Ikegami, M., Reed, J. A., Chroneos, Z. C. & Whitsett, J. A. GM-CSF regulates surfacant Protein-A and lipid catabolism by alveolar macrohpages. *Am J Physiol Lung Cell Mol Physiol* 280, L379-L386 (2001).

60 Berclaz, P. Y., Shibata, Y., Whitsett, J. A. & Trapnell, B. C. GM-CSF, via PU.1, regulates alveolar macrophage Fcgamma R-mediated phagocytosis and the IL-18/IFN-gamma - mediated molecular connection between innate and adaptive immunity in the lung. *Blood* 100, 4193-4200, doi:10.1182/blood-2002-04-1102 2002-04-1102 [pii] (2002).

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating a condition selected from hereditary pulmonary alveolar proteinosis (PAP), autoimmune pulmonary alveolar proteinosis (PAP), congenital PAP, and secondary PAP caused by disruption of alveolar macrophage surfactant clearance function and/or alveolar macrophage numbers, comprising the step of administering pioglitazone, or a pharmaceutically acceptable salt thereof to an individual diagnosed with or suspected of having a condition selected from hereditary pulmonary alveolar proteinosis (PAP), autoimmune pulmonary alveolar proteinosis (PAP), congenital PAP, and secondary PAP caused by disruption of alveolar macrophage surfactant clearance function and/or alveolar macrophage numbers.

2. The method of claim 1, wherein said congenital PAP is caused by a mutation in a gene selected from a gene encoding surfactant protein B, a gene surfactant protein C, a gene encoding Thyroid transcription factor 1, or a gene encoding ABCA3.

3. The method of claim 1, wherein said pioglitazone, or a pharmaceutically acceptable salt thereof is administered orally.

4. The method of claim 1, wherein said pioglitazone, or a pharmaceutically acceptable salt thereof is administered via inhalation.

5. The method of claim 1, wherein said pioglitazone, or a pharmaceutically acceptable salt thereof is administered in an amount sufficient to reduce cholesterol in alveolar macrophages.

6. The method of claim 1, wherein said pioglitazone, or a pharmaceutically acceptable salt thereof is administered in an amount sufficient to increase cholesterol clearance in alveolar macrophages.

* * * * *